United States Patent
Cooper et al.

(10) Patent No.: US 8,389,238 B2
(45) Date of Patent: Mar. 5, 2013

(54) LONG-TERM IN VIVO TRANSGENE EXPRESSION

(75) Inventors: Mark J. Cooper, Moreland Hills, OH (US); Linas Padegimas, Mayfield Heights, OH (US)

(73) Assignee: Copernicus Therapeutics, Inc., Cleveland, OH (US)

( * ) Notice: Subject to any disclaimer, the term of this patent is extended or adjusted under 35 U.S.C. 154(b) by 85 days.

(21) Appl. No.: 12/676,426

(22) PCT Filed: Sep. 12, 2008

(86) PCT No.: PCT/US2008/076177
§ 371 (c)(1),
(2), (4) Date: Mar. 4, 2010

(87) PCT Pub. No.: WO2009/036280
PCT Pub. Date: Mar. 19, 2009

(65) Prior Publication Data
US 2010/0203627 A1    Aug. 12, 2010

Related U.S. Application Data

(60) Provisional application No. 60/971,703, filed on Sep. 12, 2007, provisional application No. 60/982,852, filed on Oct. 26, 2007, provisional application No. 61/021,115, filed on Jan. 15, 2008.

(51) Int. Cl.
*C12Q 1/68* (2006.01)
*C12P 19/34* (2006.01)
*C12P 21/06* (2006.01)
*C12N 15/00* (2006.01)
*C07H 21/02* (2006.01)

(52) U.S. Cl. ......... 435/69.1; 435/6; 435/70.1; 435/91.1; 435/320.1; 536/23.1; 536/24.1; 536/24.2

(58) Field of Classification Search ............. 435/6, 91.1, 435/320.1, 455, 69.1, 70.1; 514/44; 536/23.1, 536/24.1, 24.2
See application file for complete search history.

(56) References Cited

U.S. PATENT DOCUMENTS
5,122,458 A     6/1992   Post et al.

OTHER PUBLICATIONS

Paulssen et al., "Specific antisense RNA inhibition of growth hormone production in differentiated rat pituitary tumour cells" Biochemical and Biophysical Research Communications, Academic Press Inc. Orlando, FL, US, vol. 171, No. 1, Aug. 31, 1990, pp. 293-300, XP024771355.
Yew N S et al., "Optimization of Plasmid Vectors for High-Level Expression in Lung Epithelial Cells" Human Gene Therapy, Mary Ann Liebert, New York, NY, US, vol. 8, No. 5, Mar. 20, 1997, pp. 575-584, XP000940966.
International Search Report for PCT/US2008/076177 dated Jan. 21, 2009.

*Primary Examiner* — Jane Zara
(74) *Attorney, Agent, or Firm* — Banner & Witcoff, Ltd

(57) ABSTRACT

Efficient and prolonged hCFTR expression is one of the major obstacles for cystic fibrosis lung therapy. hCFTR mRNA expression levels depend on eukaryotic expression cassette components, prokaryotic backbone elements, and the gene transfer method may also influence transcriptional silencing mechanisms. A codon-optimized and CpG-reduced human CFTR gene (CO-CFTR) was made. Various vector modifications were tested to facilitate extended duration of CO-CFTR expression. Insertion of an extended 3'BGH transcribed sequence (712 bp) in an inverted orientation produced prolonged expression of CO-CFTR expression at biologically relevant levels. Further studies revealed that prolonged CO-CFTR expression is dependant on the orientation of the extended BGH 3' BGH transcribed sequence and its transcription, is not specific to the UbC promoter, and is less dependent on other vector backbone elements.

22 Claims, 19 Drawing Sheets

Fig. 4A-4C
Fig. 4A.
Fig. 4B.
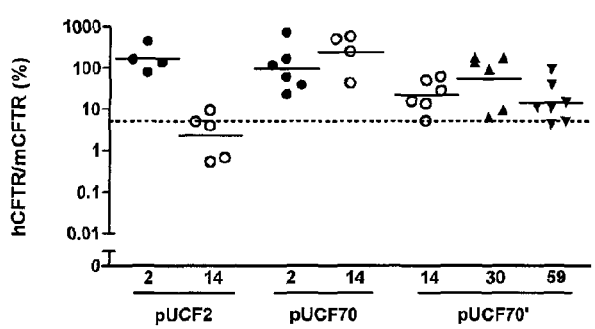
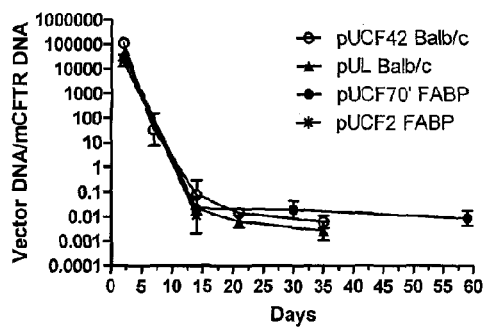
Fig. 4C.
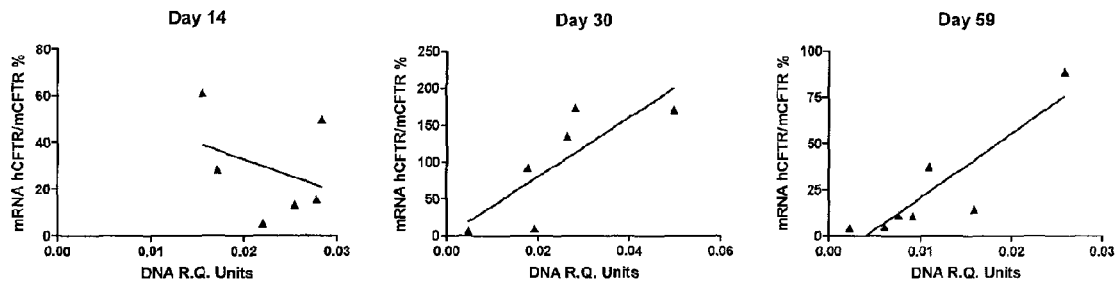

Fig. 6A-6B
Fig. 6A.
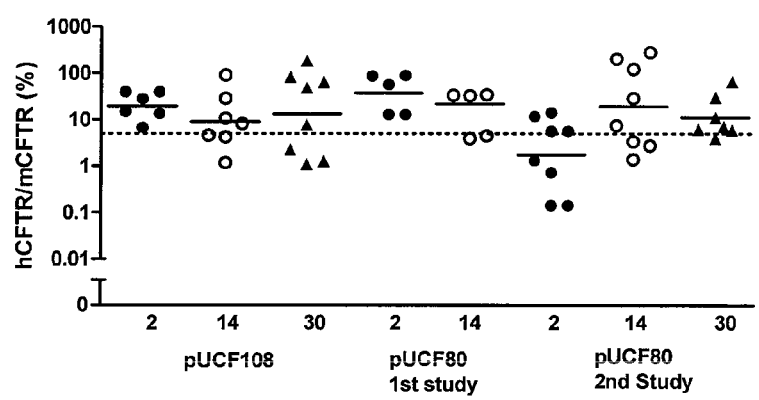
Fig. 6B.
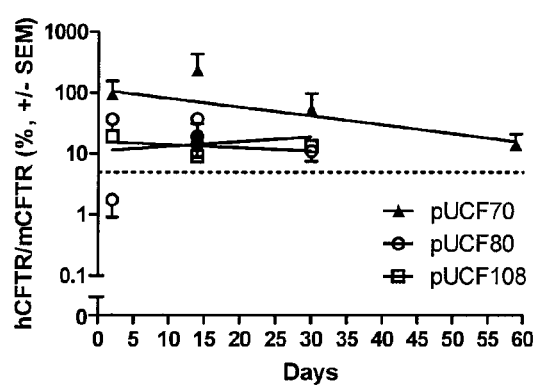

Fig. 7A-7B
Fig. 7A.
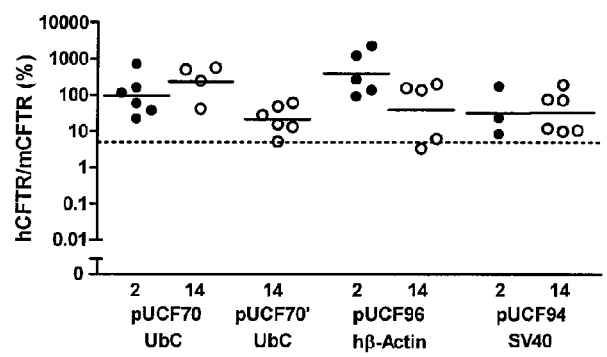
Fig. 7B.
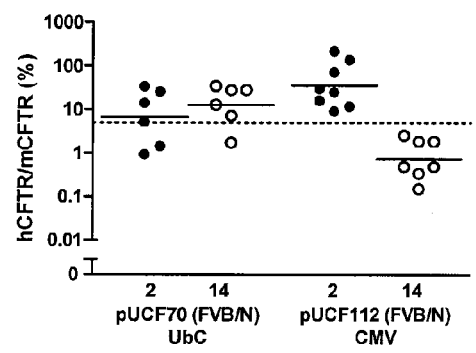

Fig. 17A
Fig. 17B
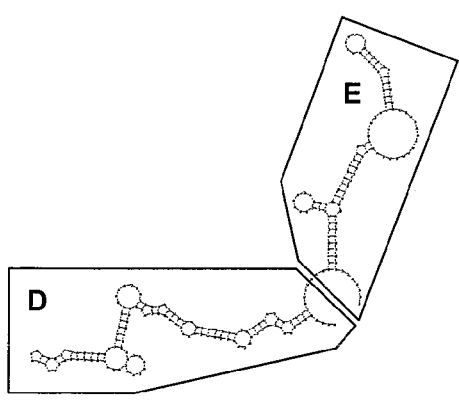
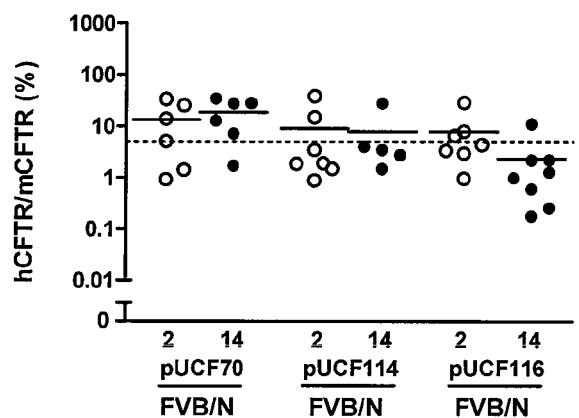

SEQUENCE LISTING

<160> NUMBER OF SEQ ID NOS: 55

<210> SEQ ID NO 1
<211> LENGTH: 132
<212> TYPE: DNA
<213> ORGANISM: Homo sapiens

<400> SEQUENCE: 1

```
agtgggagtg gcaccttcca gggtcaagga aggcacgggg gaggggcaaa caacagatgg      60
ctggcaacta gaaggcacag ctggcctccc cgaagcggcg gcacttcatg accctcaggt     120
acgtctccgt ct                                                         132
```

<210> SEQ ID NO 2
<211> LENGTH: 712
<212> TYPE: DNA
<213> ORGANISM: Homo sapiens

```
<220> FEATURE:
<221> NAME/KEY: misc_feature
<222> LOCATION: (1)...(712)
<223> OTHER INFORMATION: complement of extended BGH pA signal
<221> NAME/KEY: misc_feature
<222> LOCATION: (317)...(546)
<223> OTHER INFORMATION: complement of minimal BGH pA signal
<221> NAME/KEY: misc_feature
<222> LOCATION: (1)...(168)
<223> OTHER INFORMATION: A region
<221> NAME/KEY: misc_feature
<222> LOCATION: (169)...(466)
<223> OTHER INFORMATION: B region
<221> NAME/KEY: misc_feature
<222> LOCATION: (467)...(712)
<223> OTHER INFORMATION: C region
<221> NAME/KEY: misc_feature
<222> LOCATION: (467)...(598)
<223> OTHER INFORMATION: D region
<221> NAME/KEY: misc_feature
<222> LOCATION: (599)...(712)
<223> OTHER INFORMATION: E region
<221> NAME/KEY: misc_feature
<222> LOCATION: (534)...(712)
<223> OTHER INFORMATION: complement of 3' part of BGH ORF
<221> NAME/KEY: misc_feature
<222> LOCATION: (451)...(456)
<223> OTHER INFORMATION: AATAAA

<400> SEQUENCE: 2
aattctatga tttctatcat tacttcctca catgttggag gcatttcctc tccctctgca      60
cttaatagcc tatcttgctt taatttcttc ccactcttgg aggctaggtt tggtttggtg     120
ggctgatgag ggagggagag accgctccaa gtactttagc gggtgggatt gaaggcggag     180
ccctcctgag ctatgagtgt cctatgagtg gggctggaac taagaaccag gggcgtggac     240
agggtgtgtc acagagaagg ggatgtgcct gcttctttct ggcccaggag gaaccgggtc     300
aattcttcag cacctgggta cccatagagc ccaccgcatc cccagcatgc ctgctattgt     360
cttcccaatc ctcccccttg ctgtcctgcc ccacccacc ccccagaata gaatgacacc      420
tactcagaca atgcgatgca atttcctcat tttattagga aaggacagtg ggagtggcac     480
cttccagggt caaggaaggc acgggggagg ggcaaacaac agatggctgg caactagaag     540
gcacagctgg cctccccgaa gcggcggcac ttcatgaccc tcaggtacgt ctccgtctta     600
tgcaggtcct tccggaagca ggagagcaga ccgtagttct tgagcagcgc gtcgtcactg     660
cgcatgtttg tgtcaaattt gtcataggtc tgcttgagga tctgcccagc cc             712

<210> SEQ ID NO 3
<211> LENGTH: 4443
<212> TYPE: DNA
<213> ORGANISM: Artificial Sequence
<220> FEATURE:
<223> OTHER INFORMATION: codon optimized

<400> SEQUENCE: 3
atgcagagaa gccccctgga gaaggcctct gtggtgagca agctgttctt cagctggacc      60
agacccatcc tgagaaaggg ctacagacag agactggagc tgtctgacat ctaccagatc     120
ccctctgtgg actctgctga caacctgtct gagaagctgg agagagagtg ggacagagag     180
ctggccagca agaagaaccc caagctgatc aatgccctga gaagatgctt cttctggaga     240
ttcatgttct atggcatctt cctgtacctg ggggaggtga ccaaggctgt gcagcccctg     300
ctgctgggca gaatcattgc cagctatgac cctgacaaca aggaggagag aagcattgcc     360
atctacctgg gcattggcct gtgcctgctg ttcattgtga gaaccctgct gctgcaccct     420
gccatctttg gcctgcacca cattggcatg cagatgagaa ttgccatgtt cagcctgatc     480
```

```
tacaagaaga ccctgaagct gagcagcaga gtgctggaca agatcagcat tggccagctg    540
gtgagcctgc tgagcaacaa cctgaacaag tttgatgagg gcctggccct ggcccacttt    600
gtgtggattg ccccctgca gtggccctg ctgatgggcc tgatctggga gctgctgcag     660
gcctctgcct tctgtggcct gggcttcctg attgtgctgg ccctgttcca ggctggcctg    720
ggcagaatga tgatgaagta cagagaccag agagctggca agatctctga gagactggtg    780
atcacctctg agatgattga gaacatccag tctgtgaagg cctactgctg ggaggaggcc    840
atggagaaga tgattgagaa cctgagacag acagagctga agctgaccag aaaggctgcc    900
tatgtgagat acttcaacag ctctgccttc ttcttctctg gcttctttgt ggtgttcctg    960
tctgtgctgc cctatgccct gatcaagggc atcatcctga aaagatctt caccaccatc    1020 agcttctgca ttgtgctgag aatggctgtg accagacagt tccctgggc tgtgcagacc    1080 tggtatgaca gcctgggggc catcaacaag atccaggact tcctgcagaa gcaggagtac    1140
aagaccctgg agtacaacct gaccaccaca gaggtgtgta tggagaatgt gacagccttc    1200
tgggaggagg gctttgggga gctgtttgag aaggccaagc agaacaacaa caacagaaag    1260
accagcaatg gggatgacag cctgttcttc agcaacttca gcctgctggg cacccctgtg    1320
ctgaaggaca tcaacttcaa gattgagaga ggccagctgc tggctgtggc tggcagcaca    1380
ggggctggca gaccagcct gctgatgatg atcatggggg agctggagcc ctctgagggc    1440
aagatcaagc actctggcag aatcagcttc tgcagccagt tcagctggat catgcctggc    1500
accatcaagg agaacatcat ctttggggtg agctatgatg agtacagata cagatctgtg    1560
atcaaggcct gccagctgga ggaggacatc agcaagtttg ctgagaagga caacattgtg    1620
ctgggggagg ggggcatcac cctgtctggg gccagagag ccagaatcag cctggccaga    1680
gctgtgtaca aggatgctga cctgtacctg ctggacagcc cctttggcta cctggatgtg    1740
ctgacagaga aggagatctt tgagagctgt gtgtgcaagc tgatggccaa caagaccaga    1800
atcctggtga ccagcaagat ggagcacctg aagaaggctg acaagatcct gatcctgcat    1860
gagggcagca gctacttcta tggcaccttc tctgagctgc agaacctgca gcctgacttc    1920
agcagcaagc tgatgggctg tgacagcttt gaccagttct ctgctgagag aagaaacagc    1980
atcctgacag agaccctgca cagattcagc ctggaggggg atgcccctgt gagctggaca    2040
gagaccaaga agcagagctt caagcagaca gggagtttg gggagaagag aaagaacagc    2100
atcctgaacc ccatcaacag catcagaaag ttcagcattg tgcagaagac ccccctgcag    2160
atgaatggca ttgaggagga ctctgatgag ccctggaga aagactgag cctggtgcct    2220 gactctgagc aggggaggc catcctgccc agaatctctg tgatcagcac aggccccacc    2280
ctgcaggcca aagaagaca gtctgtgctg aacctgatga cccactctgt gaaccagggc    2340
cagaacatcc acagaaagac cacagccagc accagaaagg tgagcctggc ccccaggcc    2400 aacctgacag agctggacat ctacagcaga agactgagcc aggagacagg cctggagatc    2460
tctgaggaga tcaatgagga ggacctgaag gagtgcttct tgatgacat ggagagcatc    2520 cctgctgtga ccacctggaa cacctacctg agatacatca cagtgcacaa gagcctgatc    2580
tttgtgctga tctggtgcct ggtgatcttc ctggctgagg tggctgccag cctggtggtg    2640
ctgtggctgc tgggcaacac ccccctgcag gacaagggca cagcaccca gcagaaaac    2700 aacagctatg ctgtgatcat caccagcacc agcagctact atgtgttcta catctatgtg    2760
ggggtggctg acaccctgct ggccatgggc ttcttcagag gctgccccct ggtgcacacc    2820
ctgatcacag tgagcaagat cctgcaccac aagatgctgc actctgtgct gcaggccccc    2880
```

```
atgagcaccc tgaacaccct gaaggctggg ggcatcctga acagattcag caaggacatt    2940
gccatcctgg atgacctgct gccctgacc atctttgact tcatccagct gctgctgatt     3000
gtgattgggg ccattgctgt ggtggctgtg ctgcagccct acatctttgt ggccacagtg    3060
cctgtgattg tggccttcat catgctgaga gcctacttcc tgcagaccag ccagcagctg    3120
aagcagctgg agtctgaggg cagaagcccc atcttcaccc acctggtgac cagcctgaag    3180
ggcctgtgga ccctgagagc cttggcaga cagccctact tgagaccct gttccacaag     3240 gccctgaacc tgcacacagc caactggttc ctgtacctga gcaccctgag atggttccag    3300
atgagaattg agatgatctt tgtgatcttc ttcattgctg tgaccttcat cagcatcctg    3360
accacagggg aggggagggcagagtgggc atcatcctga ccctggccat gaacatcatg     3420
agcaccctgc agtgggctgt gaacagcagc attgatgtgg acagcctgat gagatctgtg    3480
agcagagtgt tcaagttcat tgacatgccc acagagggca agcccaccaa gagcaccaag    3540
ccctacaaga atggccagct gagcaaggtg atgatcattg agaacagcca tgtgaagaag    3600
gatgacatct ggccctctgg gggccagatg acagtgaagg acctgacagc caagtacaca    3660
gaggggggca atgccatcct ggagaacatc agcttcagca tcagccctgg ccagagagtg    3720
ggcctgctgg gcagaacagg ctctggcaag agcaccctgc tgtctgcctt cctgagactg    3780
ctgaacacag agggggagat ccagattgat ggggtgagct gggacagcat cacccctgcag   3840 cagtggagaa aggcctttgg ggtgatcccc cagaaggtgt tcatcttctc tggcaccttc    3900
agaaagaacc tggaccccta tgagcagtgg tctgaccagg agatctggaa ggtggctgat    3960
gaggtgggcc tgagatctgt gattgagcag ttccctggca agctggactt tgtgctggtg    4020
gatgggggct gtgtgctgag ccatggccac aagcagctga tgtgcctggc cagatctgtg    4080
ctgagcaagg ccaagatcct gctgctggat gagccctctg cccacctgga ccctgtgacc    4140
taccagatca tcagaagaac cctgaagcag gcctttgctg actgcacagt gatcctgtgt    4200
gagcacagaa ttgaggccat gctggagtgc cagcagttcc tggtgattga ggagaacaag    4260
gtgagacagt atgacagcat ccagaagctg ctgaatgaga aagcctgtt cagacaggcc     4320 atcagcccct ctgacagagt gaagctgttc ccccacagaa acagcagcaa gtgcaagagc    4380
aagccccaga ttgctgccct gaaggaggag accgaggagg aggtgcagga caccagactg    4440
tga                                                                  4443

<210> SEQ ID NO 4
<211> LENGTH: 4443
<212> TYPE: DNA
<213> ORGANISM: Artificial Sequence
<220> FEATURE:
<223> OTHER INFORMATION: Synthetic

<400> SEQUENCE: 4
atgcagagaa gcccctggga aaggccagt gtggtgagca agcttttttt ttcctggacc       60
agacccatcc tgagaaaggg ctacagacag agactggagc tgagtgacat ctaccagatc      120
cccagtgtgg acagtgctga caacctgagt gagaagctgg agagagagtg ggacagagag      180
ctggcctcaa aaaaaaaccc caagctgatc aatgccctga aagatgtttt ttttggaga       240 ttcatgttct atggcatttt tttgtacctg ggggaggtga ccaaggctgt gcagcccctt      300
cttctgggca gaatcattgc cagctatgac cctgacaaca aggaggagag aagcattgcc     360
atctacctgg gcattggcct gtgccttctg ttcattgtga gaacccttct tctgcaccct     420
gccatctttg gcctgcacca cattggcatg cagatgagaa ttgccatgtt cagcctgatc    480
```

```
tataaaaaaa ccctgaagct gagctccaga gtgctggaca agatcagcat tggccaactg    540
gtgagccttc tgagcaacaa cctgaacaag tttgatgagg gcctggccct ggcccacttt    600
gtgtggattg cccccccttca ggtggccctt ctgatgggcc tgatctggga gcttcttcag    660
gccagtgcct tctgtggcct gggttttttg attgtgctgg ccctgttcca ggccggcctg    720
ggcagaatga tgatgaagta cagagaccag agagctggca agatcagtga gagactggtg    780
atcaccagtg agatgattga gaacatccag agtgtgaagg cctactgttg ggaggaggcc    840
atggaaaaaa tgattgagaa cctgagacag acagagctga agctgaccag aaaggctgcc    900
tatgtgagat acttcaactc cagtgctttt ttttttttctg gttttttttgt ggttttttttg    960 agtgtgctgc cctatgccct gatcaagggc atcatcctga gaaagatctt caccaccatc    1020
agcttctgca ttgtgctgag aatggctgtg accagacagt tcccctgggc tgtgcagacc    1080
tggtatgaca gcctgggggc catcaacaag atccaggatt ttttgcagaa gcaggagtac    1140
aagaccctgg agtacaacct gaccaccaca gaggtggtga tggagaatgt gacagccttc    1200
tgggaggagg gctttgggga gctgtttgag aaggccaagc agaacaacaa caacagaaag    1260
accagcaatg gggatgacag cctttttttt tctaacttca gccttctggg cacccctgtg    1320
ctgaaggaca tcaacttcaa gattgagaga ggccaacttc tggctgtggc tggcagcaca    1380
ggggctggca gaccagcct tctgatgatg atcatggggg agctggagcc cagcgagggc    1440
aagatcaagc acagtggcag aatcagcttc tgtagccagt tctcctggat catgcctggc    1500
accatcaagg agaacatcat ctttggggtg agctatgatg agtaccggta ccggagcgtg    1560
atcaaggcct gccaactgga ggaggacatc agcaagtttg ctgagaagga caacattgtg    1620
ctgggggagg ggggcatcac cctgagcggg gccagcgggg cccggatcag cctggccagg    1680
gccgtgtaca aggatgctga cctgtacctt ctggacagcc cctttggcta cctggatgtg    1740
ctgacagaga aggagatctt tgagagctgt gtgtgcaagc tgatggccaa caagaccaga    1800
atcctggtga ccagcaagat ggagcactta aaaaaagctg acaagatcct gatcctgcat    1860
gagggctcca gctacttcta tggcaccttc agtgagcttc agaaccttca gcctgacttc    1920
tccagcaagc tgatgggctg tgacagcttt gaccagttca gtgctgagag aagaaacagc    1980
atcctgacag agaccctgca cagattcagc ctggaggggg acgcccccgt gagctggaca    2040
gagacaaaaa aacagagctt caagcagaca ggggagtttg gggaaaaaag aaaaaacagc    2100
atcctgaacc ccatcaacag catcagaaag ttcagcattg tgcaaaaaac ccccccttcag    2160 atgaatggca ttgaggagga cagtgatgag ccccctggaga aagactgag cctggtgcct    2220 gacagtgagc aggggggaggc catcctgccc agaatcagtg tgatcagcac aggccccacc    2280
cttcaggcca ggcggaggca gagtgtgctg aacctgatga cccacagtgt gaaccagggc    2340
cagaacatcc acagaaagac cacagccagc accagaaagg tgagcctggc cccccaggcc    2400
aacctgacag agctggacat ctactccaga agactgagcc aggagacagg cctggagatc    2460
agtgaggaga tcaatgagga ggacctgaag gagtgttttt ttgatgacat ggagagcatc    2520
cctgccgtga ccacctggaa cacctacctg agatacatca cagtgcacaa gagcctgatc    2580
tttgtgctga tctggtgcct ggtgattttt ttggctgagg tggctgccag cctggtggtg    2640
ctgtggcttc tgggcaacac ccccccttcag gacaagggca cagcacccca ctccagaaac    2700
aacagctatg ctgtgatcat caccagcacc tccagctact atgttttttta catctatgtg    2760 ggggtggctg acacccttct ggccatgggt ttttccggg gcctgcccct ggtgcacacc    2820
ctgatcacag tgagcaagat cctgcaccac aagatgctgc acagtgtgct tcaggccccc    2880
```

-continued

```
atgagcaccc tgaacaccct gaaggctggg ggcatcctga acagattcag caaggacatt    2940
gccatcctgg atgaccttct gccCctgacc atctttgact tcatccaact tcttctgatt    3000
gtgattgggg ccattgctgt ggtggctgtg cttcagccct acatctttgt ggccaccgtg    3060
cccgtgattg tggccttcat catgctgaga gcctattttt tgcagaccag ccaacaactg    3120
aagcaactgg agagtgaggg cagaagcccc atcttcaccc acctggtgac cagcctgaag    3180
ggcctgtgga ccctgagagc cttcggcagg cagccctact tgagaccct gttccacaag    3240 gccctgaacc tgcacacagc caactggttc ctgtacctga gcaccctgag atggttccag    3300
atgagaattg agatgatctt tgtgattttt tttattgctg tgaccttcat cagcatcctg    3360
accacagggg aggggaggg caggtgggc atcatcctga ccctggccat gaacatcatg    3420
agcacccttc agtgggctgt gaactccagc attgatgtgg acagcctgat gagaagtgtg    3480
agcagagtgt tcaagttcat tgacatgccc accgagggca agcccaccaa gagcaccaag    3540
ccctacaaga atggccaact gagcaaggtg atgatcattg agaacagcca tgtaaaaaaa    3600
gatgacatct ggcccagcgg gggccagatg acagtgaagg acctgacagc caagtacaca    3660 gagggggggca atgccatcct ggagaacatc agcttcagca tcagccccgg ccagcgggtg    3720
ggccttctgg gccggaccgg cagcggcaag agcacccttc tgagtgcttt tttgagactt    3780
ctgaacacag aggggggagat ccagattgat ggggtgagct gggacagcat cacccttcaa    3840
cagtggagaa aggcctttgg ggtgatcccc cagaaggtgt tcattttttc tggcaccttc    3900
agaaaaaatc tggaccccta tgagcagtgg agtgaccagg gatctggaa ggtggctgat    3960 gaggtgggcc tgcggagcgt gattgagcag ttccctggca agctggactt tgtgctggtg    4020
gatgggggct gtgtgctgag ccatggccac aagcaactga tgtgcctggc cagaagtgtg    4080
ctgagcaagg ccaagatcct tcttctggat gagcccagtg cccacctgga ccctgtgacc    4140
taccagatca tcagaagaac cctgaagcag gcctttgctg actgcacagt gatcctgtgt    4200
gagcacagaa ttgaggccat gctggagtgc caacagttcc tggtgattga ggagaacaag    4260
gtgagacagt atgacagcat ccagaagctt ctgaatgaga gaagcctgtt cagacaggcc    4320
atcagcccca gcgaccgggt gaagctgttc ccccacagaa actccagcaa gtgcaagagc    4380 aagcccccaga ttgctgccct gaaggaggag acagaggagg aggtgcagga caccagactg    4440
tga                                                                  4443
```

```
<210> SEQ ID NO 5
<211> LENGTH: 246
<212> TYPE: DNA
<213> ORGANISM: Homo sapiens

<400> SEQUENCE: 5
agtgggagtg gcaccttcca gggtcaagga aggcacgggg gaggggcaaa caacagatgg     60
ctggcaacta gaaggcacag ctggcctccc cgaagcggcg gcacttcatg accctcaggt    120
acgtctccgt cttatgcagg tccttccgga agcaggagag cagaccgtag ttcttgagca    180
gcgcgtcgtc actgcgcatg tttgtgtcaa atttgtcata ggtctgcttg aggatctgcc    240
cagccc                                                               246
```

```
<210> SEQ ID NO 6
<211> LENGTH: 31
<212> TYPE: DNA
<213> ORGANISM: Artificial Sequence
<220> FEATURE:
<223> OTHER INFORMATION: Primer
```

```
<400> SEQUENCE: 6
atacaccatg gaggatgcca agaatattaa g                              31

<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7
atacaactag tctagattat ttgccaccct tcttggcct                      39

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
acatatctag actgcaggcc tccgcgccgg gttttg                         36

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
gtcttccatg gtggctagct cgtctaaca                                 29

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10
atatctctag aaattctatg atttctatca ttacttc                        37

<210> SEQ ID NO 11
<211> LENGTH: 38
<212> TYPE: DNA
<213> ORGANISM: Artificial Sequence
<220> FEATURE:
<223> OTHER INFORMATION: Primer

<400> SEQUENCE: 11
gtgaacatat tgactcaatt gggctgggca gatcctca                       38

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
tgaggatctg cccagcccaa ttgagtcaat atgttcac                       38

<210> SEQ ID NO 13
<211> LENGTH: 30
```

-continued

<212> TYPE: DNA
<213> ORGANISM: Artificial Sequence
<220> FEATURE:
<223> OTHER INFORMATION: Primer

<400> SEQUENCE: 13
tatggtatga catatgggtt ccctttatt                                     30

<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14
acataactag tgctagccag acatgataag atacattg                           38

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
gaatttctag accataccac atttgtagag gttttac                            37

<210> SEQ ID NO 16
<211> LENGTH: 39
<212> TYPE: DNA
<213> ORGANISM: Artificial Sequence
<220> FEATURE:
<223> OTHER INFORMATION: Primer

<400> SEQUENCE: 16
cttgacgagt tcttctgaca tgtgagcaaa aggccagca                          39

<210> SEQ ID NO 17
<211> LENGTH: 35
<212> TYPE: DNA
<213> ORGANISM: Artificial Sequence
<220> FEATURE:
<223> OTHER INFORMATION: Primer

<400> SEQUENCE: 17
gatatcatga ccaaaatccc ttaacgtgag ttttc                              35

<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18
tgctggcctt ttgctcacat gtcagaagaa ctcgtcaag                          39

<210> SEQ ID NO 19
<211> LENGTH: 37
<212> TYPE: DNA
<213> ORGANISM: Artificial Sequence
<220> FEATURE:
<223> OTHER INFORMATION: Primer

<400> SEQUENCE: 19
acaattaatt aattgacaat taatcatcgg catagta                            37

<210> SEQ ID NO 20
<211> LENGTH: 37
<212> TYPE: DNA
<213> ORGANISM: Artificial Sequence
<220> FEATURE:
<223> OTHER INFORMATION: Primer

<400> SEQUENCE: 20
acatatctag acaattaatt aattgacaat taatcat                       37

<210> SEQ ID NO 21
<211> LENGTH: 35
<212> TYPE: DNA
<213> ORGANISM: Artificial Sequence
<220> FEATURE:
<223> OTHER INFORMATION: Primer

<400> SEQUENCE: 21
tattgtctag atatcatgac caaaatccct taacg                         35

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
ctagcaagct taattaagga tccat                                    25

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
ggatccttaa ttaagcttg                                           19

<210> SEQ ID NO 24
<211> LENGTH: 34
<212> TYPE: DNA
<213> ORGANISM: Artificial Sequence
<220> FEATURE:
<223> OTHER INFORMATION: Primer

<400> SEQUENCE: 24
ttaatggatc cagacatgat aagatacatt gatg                          34

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
tgcaggaatt ccataccaca tttgtagagg ttttac                        36

<210> SEQ ID NO 26
<211> LENGTH: 37
<212> TYPE: DNA
<213> ORGANISM: Artificial Sequence
<220> FEATURE:
<223> OTHER INFORMATION: Primer

```
<400> SEQUENCE: 26
gatatctcta gattgacaat taaacattgg catagta                              37

<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27
aaggttttaa ggtttcctag gttatcctca gtc                                 33

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
tctgacgtgg cagcgctcgc cgtga                                          25

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
acatatctag aattcaagat cagcagttca acctg                               35

<210> SEQ ID NO 30
<211> LENGTH: 36
<212> TYPE: DNA
<213> ORGANISM: Artificial Sequence
<220> FEATURE:
<223> OTHER INFORMATION: Primer

<400> SEQUENCE: 30
aattaatgca tccagacatg ataagataca ttgatg                              36

<210> SEQ ID NO 31
<211> LENGTH: 37
<212> TYPE: DNA
<213> ORGANISM: Artificial Sequence
<220> FEATURE:
<223> OTHER INFORMATION: Primer

<400> SEQUENCE: 31
ttaatatgca tccataccac atttgtagag gttttac                             37

<210> SEQ ID NO 32
<211> LENGTH: 38
<212> TYPE: DNA
<213> ORGANISM: Artificial Sequence
<220> FEATURE:
<223> OTHER INFORMATION: Primer

<400> SEQUENCE: 32
atatctctag agagtcaata tgttcacccc aaaaaagc                            38

<210> SEQ ID NO 33
<211> LENGTH: 39
```

<212> TYPE: DNA
<213> ORGANISM: Artificial Sequence
<220> FEATURE:
<223> OTHER INFORMATION: Primer

<400> SEQUENCE: 33
tgatatctag aggatccaca gatgttactt agccttta                                    39

<210> SEQ ID NO 34
<211> LENGTH: 36
<212> TYPE: DNA
<213> ORGANISM: Artificial Sequence
<220> FEATURE:
<223> OTHER INFORMATION: Primer

<400> SEQUENCE: 34
ttcctgcagg atccaggcag gcagaagtat gcaaag                                      36

<210> SEQ ID NO 35
<211> LENGTH: 37
<212> TYPE: DNA
<213> ORGANISM: Artificial Sequence
<220> FEATURE:
<223> OTHER INFORMATION: Primer

<400> SEQUENCE: 35
cggctgcgac ggaactcgaa aatggatatc caagctc                                     37

<210> SEQ ID NO 36
<211> LENGTH: 38
<212> TYPE: DNA
<213> ORGANISM: Artificial Sequence
<220> FEATURE:
<223> OTHER INFORMATION: Primer

<400> SEQUENCE: 36
gagcttggat atccattttc gagttccgtc gcagccgg                                    38

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
cttggcatcc tccatggtgg ctagctcgtc                                             30

<210> SEQ ID NO 38
<211> LENGTH: 34
<212> TYPE: DNA
<213> ORGANISM: Artificial Sequence
<220> FEATURE:
<223> OTHER INFORMATION: Primer

<400> SEQUENCE: 38
atacacaatt gccagacatg ataagataca ttga                                        34

<210> SEQ ID NO 39
<211> LENGTH: 34
<212> TYPE: DNA
<213> ORGANISM: Artificial Sequence
<220> FEATURE:
<223> OTHER INFORMATION: Primer

<400> SEQUENCE: 39
agaaacaatt gaattccata ccacatttgt agag                                        34

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
tgtgctgagc aaggccaag                                                  19

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
cagggttctt ctgatgatct ggtag                                           25

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
ctctgcccac ctggaccctg tga                                             23

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
ctagtccatt cccagaaccc at                                              22

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
gggatccacc tgtctctgtg tc                                              22

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
aggcatttcc catgcttcta acccca                                          26

<210> SEQ ID NO 46
<211> LENGTH: 22
<212> TYPE: DNA
<213> ORGANISM: Artificial Sequence
<220> FEATURE:
<223> OTHER INFORMATION: Primer

```
<400> SEQUENCE: 46
tggcctccaa ggagtaagaa ac                                              22

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gggatagggc ctctcttgct                                                 20

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
accacccacc ccagcaagga cac                                             23

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
ctccactgga ctgcccaaag                                                 20

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
gcagtgtcag ggatgatctc ct                                              22

<210> SEQ ID NO 51
<211> LENGTH: 22
<212> TYPE: DNA
<213> ORGANISM: Artificial Sequence
<220> FEATURE:
<223> OTHER INFORMATION: Primer

<400> SEQUENCE: 51
gattgagcca tgccagagac cc                                              22

<210> SEQ ID NO 52
<211> LENGTH: 817
<212> TYPE: DNA
<213> ORGANISM: Homo sapiens

<400> SEQUENCE: 52
ttccaggatc ccaggaccca gttcaccaga cgactcaggg tcctgtggac agctcaccag     60
ctatgatggc tgcaggcccc cggacctccc tgctcctggc tttcgccctg ctctgcctgc    120
cctggactca gtggtgggc gccttcccag ccatgtcctt gtccggcctg tttgccaacg    180
ctgtgctccg ggctcagcac ctgcatcagc tggctgctga caccttcaaa gagtttgagc    240
```

```
gcacctacat cccggaggga cagagatact ccatccagaa cacccaggtt gccttctgct    300
tctctgaaac catcccggcc cccacgggca agaatgaggc ccagcagaaa tcagacttgg    360
agctgcttcg catctcactg ctcctcatcc agtcgtggct tgggcccctg cagttcctca    420
gcagagtctt caccaacagc ttggtgtttg gcacctcgga ccgtgtctat gagaagctga    480
aggacctgga ggaaggcatc ctggccctga tgcgggagct ggaagatggc acccccggg     540 ctgggcagat cctcaagcag acctatgaca aatttgacac aaacatgcgc agtgacgacg    600
cgctgctcaa gaactacggt ctgctctcct gcttccggaa ggacctgcat aagacggaga    660
cgtacctgag ggtcatgaag tgccgccgct tcggggaggc cagctgtgcc ttctagttgc    720
cagccatctg ttgtttgccc ctcccccgtg ccttccttga ccctggaagg tgccactccc    780
actgtccttt cctaataaaa tgaggaaatt gcatcgc                             817

<210> SEQ ID NO 53
<211> LENGTH: 36
<212> TYPE: DNA
<213> ORGANISM: Artiificial sequence
<220> FEATURE:
<223> OTHER INFORMATION: primer

<400> SEQUENCE: 53
atatctctag attgaaggcg gagccctcct gagcta                               36

<210> SEQ ID NO 54
<211> LENGTH: 38
<212> TYPE: DNA
<213> ORGANISM: Artificial Sequence
<220> FEATURE:
<223> OTHER INFORMATION: Primer

<400> SEQUENCE: 54
gtgaacatat tgactcaatt gggctgggca gatcctca                             38

<210> SEQ ID NO 55
<211> LENGTH: 36
<212> TYPE: DNA
<213> ORGANISM: Artificial Sequence
<220> FEATURE:
<223> OTHER INFORMATION: Primer

<400> SEQUENCE: 55
atatctctag aagtgggagt ggcaccttcc agggtc                               36
```

LONG-TERM IN VIVO TRANSGENE EXPRESSION

TECHNICAL FIELD OF THE INVENTION

This invention is related to the area of transgene expression. In particular, it relates to methods and constructs for maintaining high level of expression of transgenes.

BACKGROUND OF THE INVENTION

Genetic replacement therapy for the lungs of cystic fibrosis (CF) patients has multiple requirements to be effective and safe, including adequate levels of hCFTR mRNA in proximal lung epithelial cells using a vector system that is non-immunogenic and non-toxic. Based on in vitro studies, observations in various strains of CF knockout mice, and correlations with human CF lung disease, there is a consensus that achieving approximately 5-10% of normal levels of hCFTR mRNA may be therapeutic [1-3]. The therapeutic challenge is to achieve this level of wildtype hCFTR mRNA in the context of gene transfer to the CF lung, where the disease process typically results in thick mucus secretions that may reduce gene transfer efficiencies.

DNA nanoparticles comprised of single molecules of DNA compacted with polyethylene glycol (PEG)-substituted lysine peptides enter the apical membrane of lung epithelial cells by binding to cell surface nucleolin, and this complex then efficiently enters the nucleus of these post-mitotic cells [4]. The small size of the DNA nanoparticles is required for entry through the nuclear membrane pore [5], although the size dimension requirements for nuclear uptake in the mouse lung appears somewhat less restrictive than in microinjection studies in cells [5, 6]. DNA nanoparticles are non-toxic and do not stimulate CpG responses in the murine lung [7], and repetitive dosing to the lungs of Balb/c mice does not reduce transgene expression [8]. When applied to the nasal mucosa of CF subjects, no adverse events were associated with the nanoparticles and 8/12 subjects had functional evidence of CFTR chloride channel function, with several in the normal range of nasal potential difference testing [9]. The payload plasmid in this initial phase I trial incorporated a CMV promoter, which rapidly shuts off in the lung [10], since only transient hCFTR expression was desired, thus permitting evaluation of potential nanoparticle toxicity without the added complexity of sustained hCFTR protein effects. In total, these encouraging findings suggest that aerosol delivery of compacted DNA nanoparticles may provide sufficient hCFTR expression to address the lung manifestations of CF.

To address anticipated difficulties in transfecting the human CF lung, optimization of the hCFTR expression plasmid to achieve high level and prolonged mRNA levels is a premium requirement, since the ability to maintain expression in successively transfected airway cells might address the mobile CF mucus environment. Since airway epithelial cells survive approximately 200 days before apoptosis [11], achieving hCFTR transgene mRNA expression for months is the desired objective. To achieve this goal, the DNA nanoparticle plasmid payload must efficiently enter airway cell nuclei and then remain transcriptionally active. Processes that might interfere with long term hCFTR transgene expression include promoter down-regulation [12], CpG methylation and/or heterochromatin formation within the transcriptional cassette [13], and loss of the expression plasmid itself. We report the successful optimization of hCFTR mRNA expression in the lungs of CF knockout mice by employing multiple strategies to affect the level and duration of hCFTR expression. Levels of hCFTR mRNA and protein expression have been significantly enhanced by the development of synthetic hCFTR expression 'genes' that optimize codon utilization, deplete CpG islands, and optimize Kozak consensus sequences. Additionally, prolonged duration of hCFTR expression has been achieved with use of a novel expression element derived from a 3' portion of transcribed sequences of the bovine growth hormone (BGH) gene. In combination, these hCFTR expression plasmids, delivered as compacted DNA nanoparticles to the lungs of CF knockout mice, achieve significant expression levels for multiple months, thereby addressing optimization goals for aerosol lung testing in CF subjects.

SUMMARY OF THE INVENTION

According to one aspect of the invention a nucleic acid molecule is provided. It comprises a 3' portion of transcribed sequence of the bovine growth hormone (BGH) gene. The 3' portion is operably linked in the nucleic acid molecule to a promoter from which transcription of the portion is initiated. The portion is, however, in inverted transcriptional orientation relative to its orientation in the BGH gene. Thus when transcription from the promoter occurs, the strand of the BGH gene which is transcribed is the complement of the strand that is transcribed in the BGH gene itself.

According to another aspect of the invention a method is provided for improving long-term expression of a transgene in a nucleic acid molecule. A 3' portion of the transcribed sequence of the bovine growth hormone (BGH) gene is inserted into the nucleic acid molecule so that it is operably linked to a promoter from which transcription of the portion is initiated. However, the portion is inserted in inverted orientation relative to its orientation in the BGH gene. Thus when transcription from the promoter occurs, the strand of the BGH gene which is transcribed is the complement of the strand that is transcribed in the BGH gene itself.

According to yet another aspect of the invention a method is provided for making a nucleic acid molecule for long-term expression of a transgene. A transgene is inserted into a nucleic acid molecule which comprises a promoter and a 3' portion of the transcribed sequence of the bovine growth hormone (BGH) gene. The transgene is inserted 3' of the promoter and 5' of the 3' portion of the transcribed sequence of the BGH gene. The 3' portion is in operably linked to the promoter in the nucleic acid. However, it is in inverted orientation relative to its orientation in the BGH gene. Thus when transcription from the promoter occurs, the strand of the BGH gene which is transcribed is the complement of the strand that is transcribed in the BGH gene itself.

These and other embodiments which will be apparent to those of skill in the art upon reading the specification provide the art with methods and nucleic acid constructs for maintaining high levels of expression of transgenes in vivo.

BRIEF DESCRIPTION OF THE DRAWINGS

(FIG. 1B) Luciferase activity in Balb/C mouse lungs on days 2 and 14 after IN dosing of ~100 µg of compacted plasmid DNA (N=9/group). This dose of DNA is at the peak linear range of a DNA dose response curve in murine lung [7]. (FIG. 1C) Plots of hCFTR/mCFTR mRNA levels in mouse lungs dosed IN with compacted pUCF and pUCF2 plasmids. pUCF contains 'natural' hCFTR cDNA whereas pUCF2 contains a codon-optimized, CpG-depleted (except 1 CpG in the 3' terminus), and 5' and 3' UTR truncated in vitro synthesized DNA. (Solid lines indicate geometric means; dotted line equals 5%.)

FIG. 4A-FIG. 4C. (FIG. 4A) Repeat pUCF70 study (pUCF70') in FABP mice. 106 µg of compacted pUCF70 was dosed IT and animals were harvested at days 14, 30, and 59 for qRT-PCR analysis. Dotted line equals 5%. (Solid lines indicate geometric means; dotted line equals 5%.) (FIG. 4B) qPCR analysis of vector DNA/mCFTR genomic DNA ratios (geometric means+/−95% CI). Shown are pUCF2 and pUCF70' results in FABP mice. The pUL and pUCF42 (derivative of pUCF2 with removed S/MARs and SV40 pA signal inserted between R6K on and polyubiquitin C (UbC) promoter) results in Balb/C mice are shown for comparison. There was no difference at day 14 comparing pUCF2 and pUCF70', or pair wise among pUCF70' samples at days 14, 30, and 59 (1-way ANOVA of log-transformed data). (FIG. 4C) Correlation plots between vector DNA/mCFTR genomic DNA (expressed as relative quotients, R.Q.) and the hCFTR/mCFTR mRNA ratio. See below for data analysis (Table 1).

FIG. 6A-FIG. 6B. (FIG. 6A) Evaluation of compacted pUCF108 and pUCF80 in FABP mice. Compacted DNA was dosed IT and animal lungs were harvested at days 2, 14, or for qRT-PCR analysis. (Solid lines indicate geometric means; dotted line equals 5%.) (FIG. 6B) Comparison of geometric mean ratios from each pUCF70, pUCF80, and pUCF108 FABP mouse study. Linear regression analysis of log-transformed data was used to generate best fit line. A statistical comparison of slope and Y intercept values using an analysis of covariance (ANCOVA) generated a non-significant difference in slope (p=0.6344) and Y intercept (p=0.08445), although the nearly 5-10 fold improvement in geometric mean ratios for pUCF70 compared to pUCF80 and pUCF108 at days 2, 14, and 30 is noteworthy. These findings suggest that pUCF70 may be superior to pUCF80 and pUCF108 if the sample size of the analysis was increased. (Dotted line equals 5%.)

FIG. 7A-FIG. 7B. Evaluation of alternative promoters in the pUCF70 vector. (Solid lines indicate geometrical means; dotted line equals 5%). (FIG. 7A). The polyubiquitin C (UbC) promoter and first intron were replaced with the human 13-actin promoter and first intron (pUCF96) or the UbC promoter was replaced with the SV40 early promoter (pUCF94). Plasmids pUCF96 (108 µg) and pUCF94 (104 µg) were dosed IT in FABP mice and harvested at days 2 and 14 for qRT-PCR analysis. For comparison are prior data with pUCF70 and the day 14 repeat pUCF70' study. There was no statistically significant difference between pUCF94 and pUCF96 (2-way ANOVA of log-transformed data). (FIG. 7B) The inverted 3' BGH transcribed sequence does not facilitate prolonged CO-CFTR mRNA expression transcriptionally controlled by the CMV promoter/enhancer and also containing CMV intron A. Compacted pUCF112 was dosed IT (113 µg) in FVB/N mice and harvested on days 2 and 14 for qRT-PCR analysis. For comparison are prior pUCF70 results in FVB/N mice.

FIG. 17A-17B (FIG. 17A) Graphic representation of subdomains 'D' and 'E,', along with their proposed single-stranded secondary structure if denatured. (FIG. 17B) qRT-PCR analysis of inverted 3' BGH transcribed sequence domains 'D' (pUCF114) and 'E' (pUCF116). Compacted pUCF114 (109 µg) and pUCF116 (113 µg) were dosed IT in FVB/N mice and harvested on days 2 and 14 for CO-CFTR and mCFTR mRNA expression analysis. For comparison are prior pUCF70 results in FVB/N mice. Dotted line equals 5%.

DETAILED DESCRIPTION OF THE INVENTION

Figure 9:
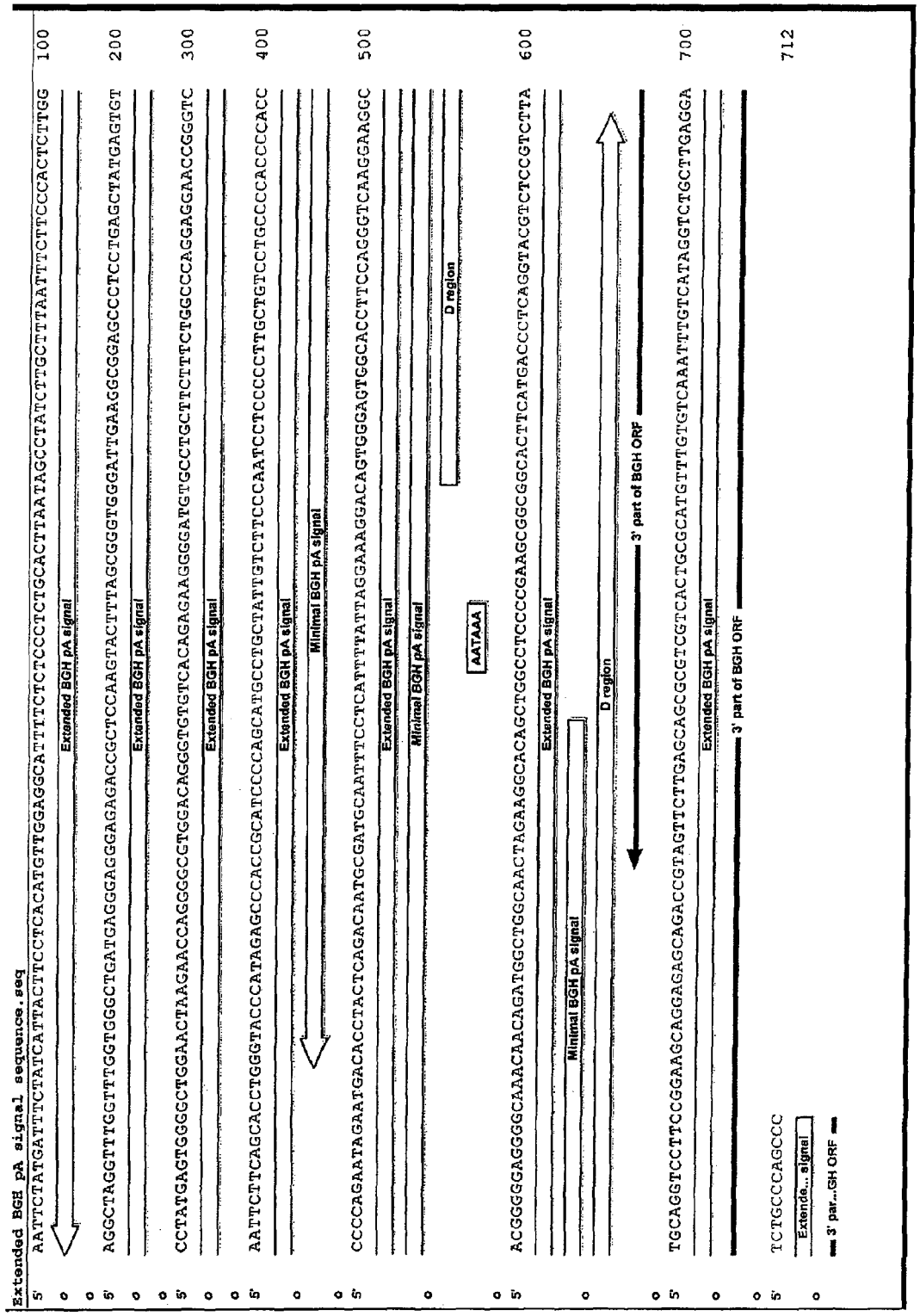
FIG. 9. Map of the extended BGH pA signal and 3' portion of transcribed BGH gene in inverted orientation. (SEQ ID NO: 2)

The inventors have developed nucleic acid constructs and methods for enhancing persistence of expression of transgenes. The inventors have found that use of a nucleic acid element that derives from the 3' end of the BGH gene in the inverted orientation prevents the drop-off in expression levels which often plagues transgene expression. Although the absolute minimal element has not been defined, it is contained within the 132 nt shown in SEQ ID NO: 1. As shown in FIG. 9, the 132 nt region (labeled as the D region) includes the 3' part of the BGH open reading frame as well as the 3' untranslated region. The minimal element does not extend beyond the end of the BGH transcribed region. The absolute minimal element may comprise only translated sequences, only untranslated sequences, or both.

The size of the BGH-derived element may vary. It may, for example, be from 50 to 150 bases in length, from 100 to 200 bases, from 100 to 1000 bases. Following the examples provided, one of skill in the art can readily test various fragments to ascertain ability to provide long-term expression.

The nucleic acid molecules as described here, may comprise ribonucleotides or deoxyribonucleotides. They may be single or double stranded. They may be linear or circular molecules. They may be expression vectors or viral vectors. The nucleic acid molecules contain at least the minimal element required to maintain expression of a transgene at approximately the same level at day 14 as is expressed at day 2. As used here, the term long-term expression indicates expression at day 14 post administration to an animal. Approximately the same level is within a factor of 10. Approximately the same level means that it does not decrease more than 10-fold, preferably less than 5 fold, and more preferably less than 2 fold. Tests for expression may be routinely performed to confirm that the BGH element leads to the prolonged expression described.

Other elements may be present in the nucleic acid molecule. Such elements include various origins of replication, drug resistance genes, additional detectable markers, and elements including but not limited to beta-globin S/MAR, interferon beta S/MAR additional promoters, enhancers, polyadenylation signals, and introns. Suitable promoters which may be used include human beta-actin, human polyubiquitin C, and SV40 early promoters.

When a transgene is present in the nucleic acid molecule it is operably linked to a promoter, as is the inverted BGH-derived element. Upon transcription from the promoter, the transgene and the BGH element are transcribed in a single transcript. Suitable transgenes for use include any therapeutic gene coding sequence such as human cystic fibrosis transmembrane conductance regulator (CFTR), or modified versions of them. One modified version of CFTR which can be used is the codon-optimized and nearly CpG-depleted version, described below. Another example is a synthetic hCFTR coding sequence in which the nucleotide sequence has been altered to minimize nucleosome formation Alternatively, the nucleic acid molecule contains no transgene, but is designed to accept a transgene as an insertion. The transgene may be inserted, for example, at a restriction endonuclease site. Use of restriction endonucleases and ligases to make an insertion in vitro is well known in the art. Other means of making insertions can be used, as are known in the art. These may employ homologous recombination, site specific insertion, transposons, etc.

Other suitable transgenes in addition to CFTR include genes important for proper functioning of lung, eye, and brain. These include various genes normally expressed in the retina (which includes photoreceptor cells, retinal pigment epithelial cells, ganglion cells), and neurons and glial cells in the brain. Mutations in multiple genes (eg. peripherin, rhodopsin, RP1, PRPF31, RPE65, PDE6B, PDE6A, USH2A, RP2, RP3, Cep290, ABCA4, BBS1, BBS2, BBS4, BBS6, BBS7, RDH, and others) cause retinitis pigmentosa, for example, and gene replacement therapy in the retina maybe therapeutic. In the brain, one particularly interesting gene is a neuroprotectant gene, GDNF (glial cell line derived neurotrophic factor), which corrects motor defects in a rat Parkinson's disease model after compacted GDNF gene transfer in the brain. Other GDNF family members include neurturin. GDNF and other neuroprotectants have therapeutic potential in treating various retinal diseases, as well. Knockout of some genes using shRNA may be therapeutic, particularly for genes having autosomal dominant mutations. See RETNET, Genes and Mapped Loci Causing Retinal Diseases at domain sph.uth.tmc.edu, all of the listed genes are incorporated expressly herein. Other genes that may be therapeutic for various brain and eye indications include glutamic acid decarboxylase, neurturin, and human aromatic 1-amino acid carboxylase for Parkinson's disease, CLN2 for Infantile Neuronal Ceroid Lipofuscinosis, CLN3 for Battens disease, nerve growth factor for Alzheimer's disease, x-linked inhibitor of apoptosis protein (XIAP) for Huntington's disease, insulin-like growth factor-1 (IGF-1), neurturin, and excitatory amino acid transporter 2 (EAAT2) for amyotrophic lateral sclerosis, neuropeptide Y for epilepsy, proenkephalin for pain, and pigmented epithelial derived factor (PEDF) and ciliary neurotrophic growth factor (CNTF) for various forms of retinitis pigmentosa.

The nucleic acid molecule may be formulated in any way which is conventional in the art. These include without limitation DNA nanoparticles, liposomes, and viral particles. In one example, the nucleic acid molecule is compacted using a polycation to form a nanoparticle. In another example, the polycation is polylysine. In another example the polycation is polylysine to which polyethylene glycol is attached.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Initial Vector Design and hCFTR Gene Optimization

Figure 1A:
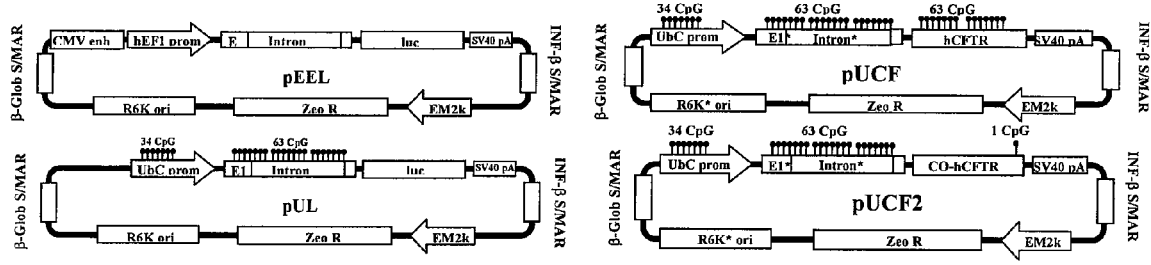
FIG. 1A-FIG. 1C (FIG. 1A) CpG-reduced and CpG-depleted vectors for luciferase and human CFTR expression.
Figure 1B:
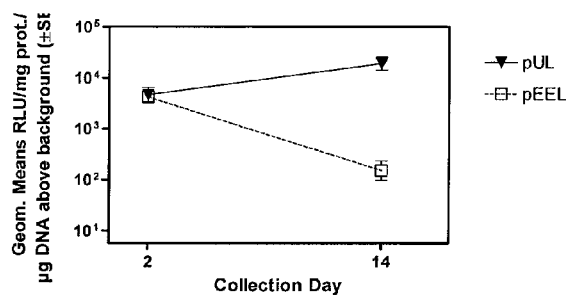

Plasmid backbone elements and expression control domains are important to optimize to produce high level and maintained transgene expression [14]. Multiple labs have reported improved expression longevity using CpG-reduced or CpG-depleted vectors [15, 16]. We prepared a completely CpG-depleted vector, pEEL, which contains a luciferase expression cassette driven by the human elongation factor 1 alpha (EF1α) promoter and terminates with an SV40 polyadenylation signal. The eukaryotic expression cassette is flanked with interferon-β and β-globin scaffold/matrix attachment domains (S/MARs) that potentially may prevent encroachment of heterochromatin formation into the eukaryotic cassette [17]. The plasmid backbone incorporates a zeocin resistance gene (ZeoR) expression cassette (FIG. 1A). Balb/c mice were dosed intranasally (IN) with compacted pEEL plasmid and lungs were harvested at days 2 and 14 to measure luciferase activity (FIG. 1B). The pEEL plasmid produced high luciferase activity on day 2 but this fell significantly by day 14 ($p<0.0001$; t test on log-transformed data).

As was published previously [18], plasmids incorporating the polyubiquitin C (UbC) promoter have been successful in generating prolonged luciferase activity in the mouse lung. To improve expression longevity, the EF1α promoter-exon-intron region was replaced with the CpG-rich UbC promoter-first exon-intron region (pUL, see FIG. 1). Compacted pUL plasmid produced similar luciferase activity as compacted pEEL on day 2 (FIG. 1B). In contrast to pEEL, luciferase activity was significantly higher on day 14 compared to day 2 in mice dosed with pUL indicating prolonged expression ($p=0.0054$; t test on log-transformed data).

The natural human cystic fibrosis transmembrane conductance regulator (hCFTR) gene cDNA sequence containing partial 5' and 3' untranslated terminal regions (UTRs) was subcloned into the pUL vector, replacing the luciferase marker gene (pUCF; see FIG. 1A). To potentially improve hCFTR expression, a synthetic hCFTR sequence (referred to as CO-CFTR) was designed, synthesized in vitro, and subcloned into the pUL backbone, forming plasmid pUCF2 (FIG. 1A). The CO-CFTR is CpG-depleted except for one CpG located close to the 3' end of the open reading frame; in contrast, the natural hCFTR cDNA in pUCF has 63 CpG islands. The synthetic CO-CFTR sequence also has a truncated 3'UTR, minimizing potential miRNA affects [19]. Overall, CO-CFTR has a 76.9% nucleotide homology to hCFTR cDNA, and potential mRNA secondary structural changes might play a role in mRNA stability. Additionally, CO-CFTR has a 55.6% GC content, whereas hCFTR cDNA has 41.6% GC content, which may be significant since increases in GC content correlate with transcriptional efficiency [20, 21]. To address potential protein expression efficiencies, this synthetic hCFTR sequence also was codon optimized, having a preferred codon usage percentage of 85.1%, significantly improved compared to the 34.6% efficiency of natural hCFTR cDNA. Lastly, CO-CFTR has a full Kozak consensus sequence (CCACCatg), whereas hCFTR cDNA (agACCatg) has only a partial match.

Figure 2:
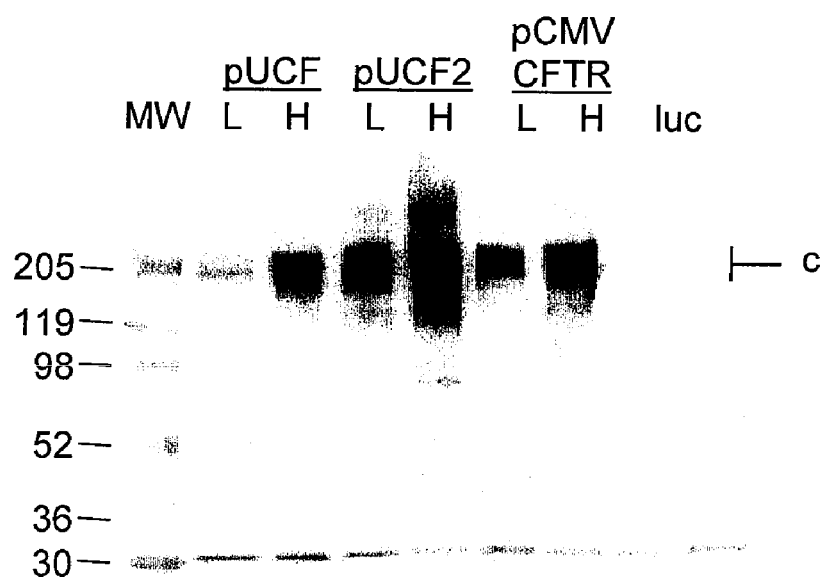
FIG. 2. IP/Western blot analysis of hCFTR expression in HEK293 cells 2 days after transfection with pUCF, pUCF2, or control pCMVCFTR plasmid. Cells were transfected with lipofectamine and either low (L, 0.75 µg) or high (H, 3 µg) amounts of CFTR plasmid. Luc, cells transfected with luciferase plasmid. NT, non-transfected. Anti-CFTR monoclonal antibody 1660 (R&D Systems), directed against R domain codons 590-830, was used in both IP and detection protocols. Similar results were noted in 3 separate experiments. Letter 'c' designates glycosylated forms of hCFTR.

CFTR-negative HEK293 cells were transfected using lipofectamine with either pUCF or pUCF2. To minimize differences in transfection efficiency between plates, each liposome/DNA transfection mixture contained an equal total amount of plasmid DNA, equal pmols of each test plasmid (but differing microgram amounts), an equal amount of luciferase plasmid (10 ng) to assess transfection efficiency, and appropriate amounts of 'filler' plasmid (Bluescript). Two days after transfection, lysates were prepared, luciferase activity assessed, and an IP/Western for CFTR performed (FIG. 2). Band densities were quantified and normalized for modest differences in luciferase activity. The Western blot showed a 9-fold increase in CFTR protein in cells transfected with pUCF2 compared to pUCF. For reference, cells were also transfected with a CMV-controlled natural hCFTR cDNA expression plasmid.

EXAMPLE 2 hCFTR mRNA Expression in the Mouse Lung: Initial Steps pUCF or pUCF2 was dosed IN into Balb/C mice and lungs were harvested at days 2 and 14 for evaluation of CFTR mRNA. qRT-PCR was performed as described in Example 7. hCFTR (or CO-CFTR) mRNA expression is presented as a hCFTR/mCFTR expression ratio multiplied by 100%.

Figure 1C:
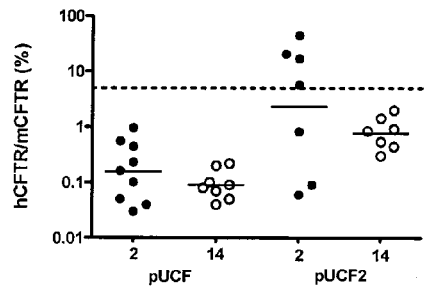

As shown in FIG. 1C, pUCF2 generated a CO-CFTR/mCFTR geometric mean ratio of 2.34% on day 2 which fell to 0.77% on day 14. The geometric mean of day 2 signal for pUCF2 was still below a biologically significant level of CFTR expression (5-10%), but four of seven animals showed higher expression than 5%. Although CFTR mRNA expression was not maintained, the hCFTR/mCFTR ratios for pUCF2 were significantly higher than pUCF (geometric mean ratio of 0.16% on day 2 and 0.09% on day 14). Interestingly, the day 2 expression for pUCF2 was considerably higher (14.6-fold) than for pUCF, which appears related to CO-CFTR since both plasmids are otherwise nearly identical.

One potential reason for transient hCFTR expression in the Balb/C mouse is immunogenicity of hCFTR. Screening of SCID and FABP (hCFTR expressed in GI tract but not in lung) mouse animal models revealed that an immune response to hCFTR is not involved in transgene expression silencing (see Example 8, FIG. 12). Neither of these strains or FABP parental strains (129, C57, and FVB/N) maintained CO-CFTR mRNA expression for two weeks. However, the FABP mouse strain produced elevated CO-CFTR expression levels (168%) on day 2 (FIG. 12) and therefore was chosen as a preferred animal model for CO-CFTR expression experiments.

EXAMPLE 3

Expression Cassette Optimization

Numerous attempts including complete CpG depletion of CO-CFTR, utilization of different natural hCFTR and synthetic introns, use of minicircles or DNA linear fragments, and other strategies failed to maintain CO-CFTR transgene mRNA expression (data not shown). Surprisingly, one pUCF2 derivative, pUCF70 (FIG. 3), containing a 3' portion of transcribed sequences of the bovine growth hormone (BGH) gene (in an inverted orientation) in the 3' UTR of CO-CFTR produced prolonged CO-CFTR expression. Elevated levels of hCFTR mRNA expression were observed at day 2 for pUCF70, comparable to prior results seen with pUCF2. Importantly, a CO-CFTR/mCFTR mRNA geometric mean ratio of 236% was observed at day 14, exceeding the expected therapeutic level of 5-10% (FIG. 4A). This study was repeated several times. In one study (designated as pUCF70' in FIG. 4A), the same dose and same lot of compacted pUCF70 (106 μg) was dosed intratracheally (IT) in three groups of FABP mice, with mRNA analysis on days 14, 30, and 59. The day 59 hCFTR/mCFTR geometric mean ratio was 14.1%, which was not statistically different than the day 30 (52.7%) or day 14 (21.3%) values (1-way ANOVA of log-transformed data). Note that the two FABP studies are presented separately and not combined, since the day 14 time points showed a significant difference (t test of log-transformed data, $p=0.0069$), perhaps reflecting differences in the biology of these two lots of mice.

To determine if the decline in CO-CFTR mRNA expression in pUCF2, or the improved persistence generated by pUCF70, is due to changes in vector DNA persistence, vector DNA was purified from dosed murine lungs and evaluated by qPCR. The significant decline in measured vector DNA in these lung samples during the first 2 weeks after gene transfer may largely reflect extracellular clearance (FIG. 4B). Destruction of DNA in the cytoplasm also may be expected. The relative plateau in observed vector DNA from day 14 to day 59 is intriguing and may reflect a progressively larger percentage of nuclear plasmid, since vector DNA in the nucleus may be relatively stable. Moreover, if the nuclear plasmid is biologically active, there may be a positive correlation between measured vector DNA and hCFTR expression. To address this possibility, correlation analysis was performed on the pUCF70' time course data (FIG. 4C).

Data for days 14, 30, and 59 were evaluated using the non-parametric Spearman's correlation test (Table 1). There was a significant correlation between CO-CFTR mRNA expression and vector DNA on days 30 and 59, but not on day 14. These findings are notable, since a positive correlation between hCFTR transgene mRNA and vector DNA in dosed lungs is certainly an anticipated relationship. The finding that this correlation is evident only at long observation intervals suggests that significant time is required to clear extra-nuclear compacted DNA, which is relatively stable in nuclease enriched environments.

TABLE 1

Correlation analysis of mRNA and vector
DNA levels in the FABP lung pUCF70
time course (study pUCF70').

| Day | Spearman r | $P_2$ value |
|---|---|---|
| 14 | −0.2000 | 0.7139 |
| 30 | 0.8857 | 0.0333 |
| 59 | 0.9286 | 0.0067 |

EXAMPLE 4 pUCF70 Vector Modifications

A series of pUCF70 derivatives (FIG. 3) were created to understand the importance of specific elements included in the vector backbone. These plasmids were tested in FABP or FVB/N mice dosed IT with approximately 100 µg of compacted DNA followed by lung collection at days 2 and 14 (and in some cases at day 30) for qRT-PCR analysis.

Figure 3A:
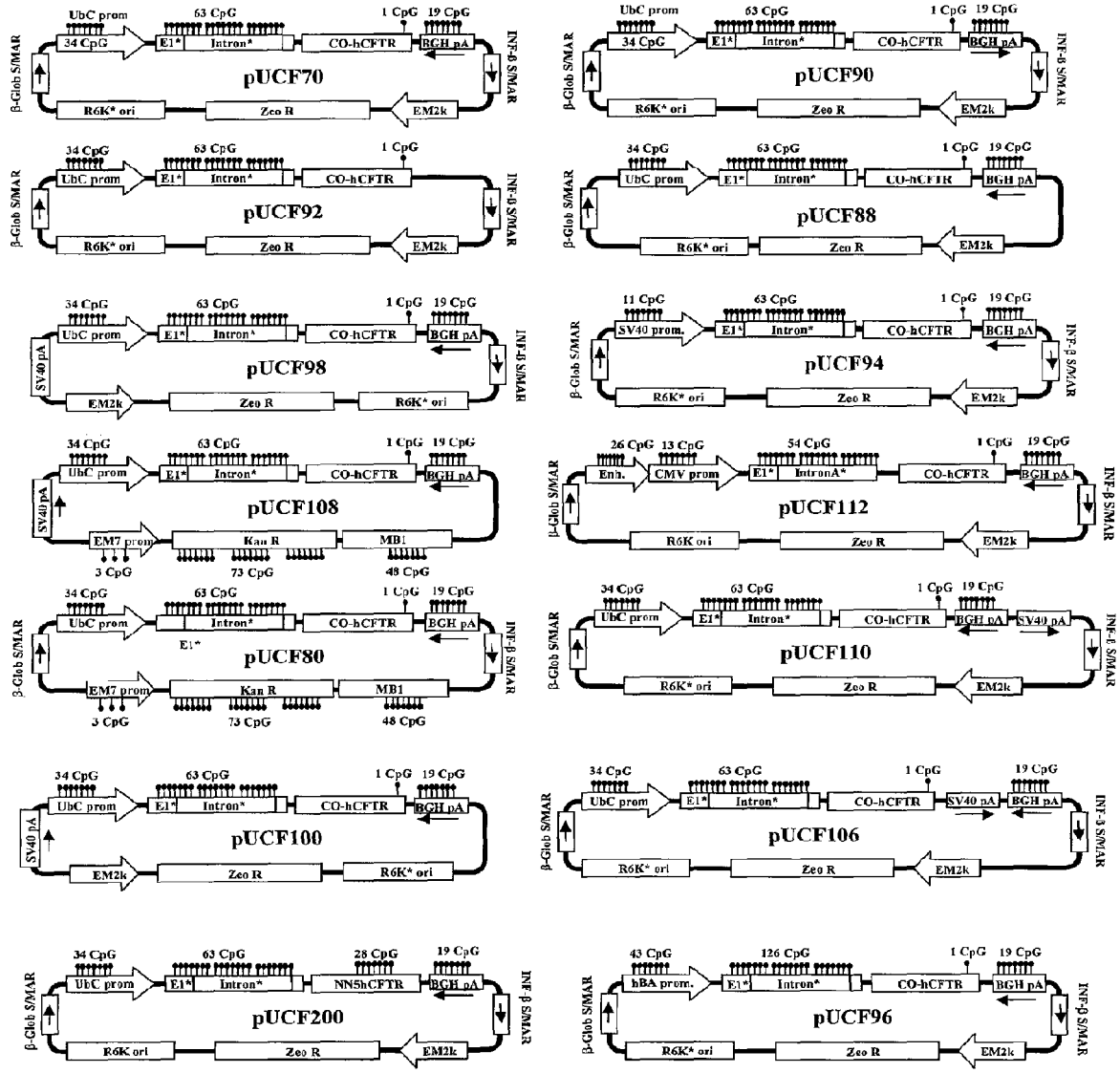
FIGS. 3A-3B. pUCF70 plasmid map and its derivatives.
Figure 3B:
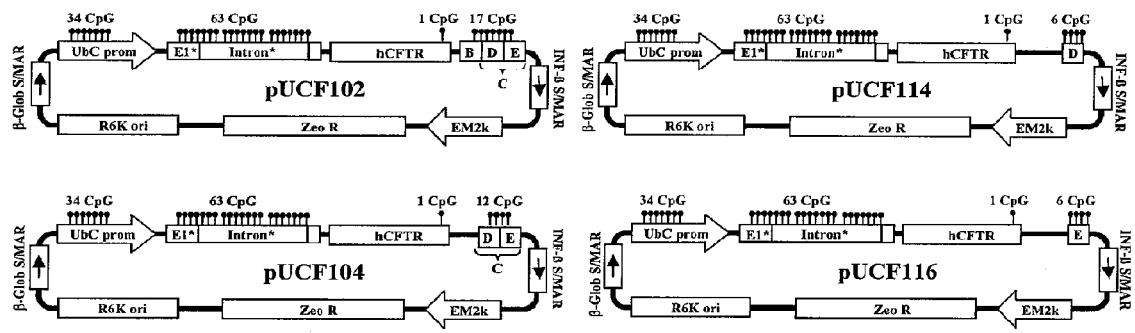
Figure 5:
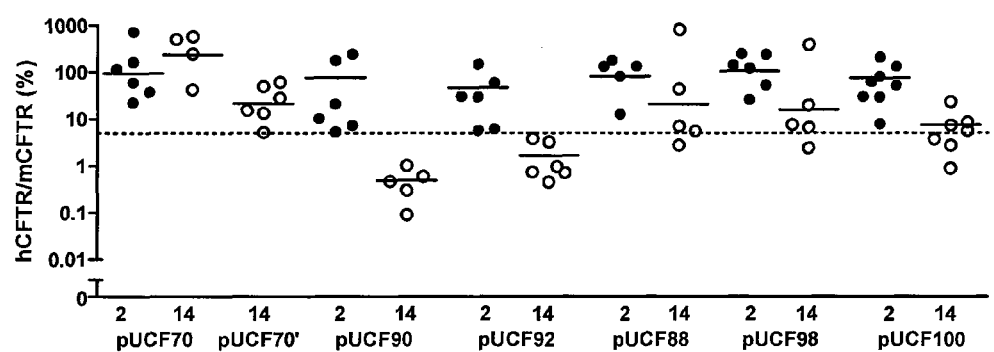
FIG. 5. Evaluation of pUCF90, pUCF92, pUCF88, pUCF98 and pUCF100 in FABP mice. Lungs were harvested at days 2 and 14 for qRT-PCR analysis of CO-CFTR expression. Prior results with pUCF70 are shown for comparison. (Solid lines indicate geometric means; dotted line equals 5%.)
Figure 13:
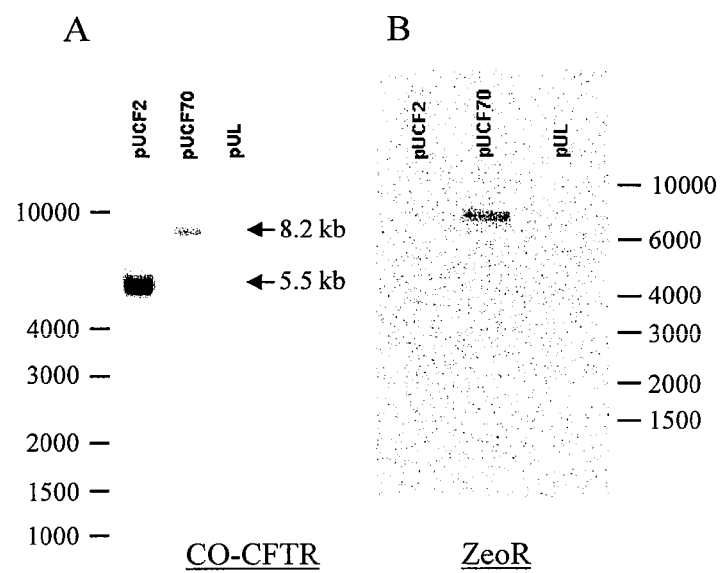
FIG. 13. Northern blot of HEK293 cells transfected with pUCF70, pUCF2 and pUL. 0.25 µg of poly A+ mRNA were loaded per lane. Hybridization probes were either a CO-CFTR fragment (A) or ZeoR (B).

Detailed pUCF70 transcript analysis revealed that plasmid backbone regions, including S/MAR sequences, are transcribed (see Example 9, FIG. 13). Since active transcription of S/MAR domains may enable episomal plasmid replication [22], pUCF70 was transfected in log phase cells, but a plasmid replication assay was negative (see Example 10, FIG. 14). Despite the failure to detect episomal plasmid replication, we speculated that active transcription of one or both S/MAR domains might be responsible for improved CO-CFTR mRNA persistence. To test this hypothesis, FABP mice were dosed IT with pUCF90 and pUCF92 (FIG. 3). If active S/MAR transcription is indeed necessary for CO-CFTR mRNA persistence, then one would predict that pUCF90, with correct orientation of the BGH pA site, would produce only transient CO-CFTR expression (comparable to pUCF2), whereas complete removal of the BGH pA site should, like pUCF70, produce persistent expression. On the other hand, if presence of the inverted 3' BGH transcribed sequence in pUCF70 DNA and/or transcription of the inverted 3' BGH transcribed sequence is necessary for persistence, then neither plasmid would show persistence. As shown in FIG. 5, pUCF90 and pUCF92 showed only transient hCFTR expression, with day 2 geometric mean ratios of 77% and 46%, which fell at day 14 to 0.5% and 1.7%, respectively.

The day 14 decline in hCFTR expression was expected for pUCF90, although the decline for pUCF92 is noteworthy and indicates that the inverted 3' BGH transcribed sequence is necessary for maintained hCFTR expression in pUCF70. To evaluate further the importance of S/MAR sequences, pUCF88 and pUCF98, which are pUCF70 derivatives that lack either the INF-β or β-globin S/MARs, were tested. The hCFTR/mCFTR mRNA geometric mean ratio for pUCF88 at days 2 and 14 were 80% and 20.6%, and for pUCF98 were 104% and 15.6% (FIG. 5). There are no statistical differences at any time point between any of these groups (2-way ANOVA of log-transformed data). It is appreciated, however, that both the pUCF88 and pUCF98 day 14 groups have a single very high expressor for unclear reasons. Overall, these findings indicate that either S/MAR appears sufficient for long-term expression, and raises the question whether transcription of any S/MAR domain is necessary.

Two pUCF70 derivatives lacking S/MARs, pUCF100 (containing ZeoR-R6K backbone) and pUCF108 (containing CpG-enriched kanamycin resistance gene (KmR)-MB1 backbone) were created and tested in FABP mice. pUCF100 generated CO-CFTR/mCFTR geometric mean ratios of 51.2% at day 2, which fell to 4.99% at day 14 (p=0.0007, t test of log-transformed data). pUCF100 is the first plasmid with an inverted 3' BGH transcribed sequence to not generate prolonged hCFTR expression (FIG. 5). These data suggest that plasmids with an inverted 3' BGH transcribed sequence require at least one S/MAR domain for maintained CO-CFTR mRNA expression.

However, another pUCF70 derivative plasmid deficient in S/MAR domains, pUCF108, produced prolonged expression. In FABP mice, pUCF108 generated a CO-CFTR/mCFTR geometric mean ratio of 19.5% on day 2, 9.00% on day 14, and 13.3% on day 30 (FIG. 6A) (not different by 1-way ANOVA of log-transformed data, p=0.6792). This experiment demonstrates that neither the CpG-depleted ZeoR-R6K backbone nor S/MAR sequences are absolutely necessary for prolonged expression. Of note, pUCF108 produced lower CO-CFTR expression levels on days 2, 14, and 30 than pUCF70 (FIG. 6B), implicating a positive S/MAR role or negative KmR-MB1 backbone influence on gene expression levels.

Another pUCF70 derivative, pUCF80, containing the KmR-MB1 backbone insulated with two S/MARs, was tested in 2 independent studies. The first study revealed encouraging results, with geometric mean CO-CFTR/mCFTR ratios of 36.8% at day 2 and 14.5% at day 14 (p=0.205, t test of log-transformed data). For unclear reasons in the second study, the day 2 results were unexpectedly low, with a CO-CFTR/mCFTR geometric mean ratio of 1.76%, although expression was higher at days 14 (19.1%) and 30 (11.0%) (FIG. 6A). The day 2 results are statistically lower than day 14 (1-way ANOVA of log-transformed data, p<0.05 by Bonferroni's multiple comparison test). Overall, data analysis did not reveal silencing. However, CO-CFTR expression levels produced by plasmids containing KmR-MB1 backbone (pUCF80 and pUCF108) were lower compared with pUCF70 (FIG. 6B; see ANCOVA analysis in legend to FIG. 6B).

To determine if the UbC promoter is necessary for pUCF70 to produce prolonged CO-CFTR mRNA expression in the FABP lung, pUCF70 derivative plasmids were prepared replacing UbC with either the human β-actin (pUCF96) or SV40 early (pUCF94) promoters. Additionally, pUCF96 has replaced the UbC first intron with the human β-actin first intron; the UbC first intron remains intact in pUCF94. These plasmids were compacted and dosed IT in FABP mice, and lungs were harvested at days 2 and 14 (FIG. 7A). pUCF96 generated very high day 2 CO-CFTR expression, with a geometric mean ratio of 398% which fell 10-fold to 39.5% by day 14. This reduction had near statistical significance (t test of log-transformed data, p=0.0653). pUCF94 generated hCFTR/mCFTR geometric mean ratios of 33.0% on day 2 and 33.6% on day 14. This difference was not significant. In summary, these data with pUCF96 and pUCF94 suggest that the UbC promoter can be replaced by other promoters in the pUCF70 vector and still achieve maintained expression at day 14, although the near significance of the pUCF96 reduction suggests that further study is required to address this point with more certainty.

Since the CMV promoter/enhancer is well-described to produce transient expression in the mouse lung [7, 23], we sought to determine if prolonged expression could be achieved by including the inverted 3' BGH transcribed sequence. Vector pUCF112 is a derivative of pUCF70 in which the UbC promoter and first intron are replaced with the CMV promoter, enhancer, and intron A. pUCF112 was dosed in FVB/N mice and qRT-PCR analysis was performed at days 2 and 14 (FIG. 7B). Only transient expression was observed, with a CO-CFTR/mCFTR geometric mean ratio of 35.8% on day 2 and 0.72% on day 14 (p<0.0001, t test of log-transformed data).

In summary, these promoter studies reveal that prolonged CO-CFTR mRNA expression mediated by the inverted 3' BGH transcribed sequence is not restricted to the UbC promoter, although it may not enable prolonged expression with some promoters, such as CMV.

Figure 8:
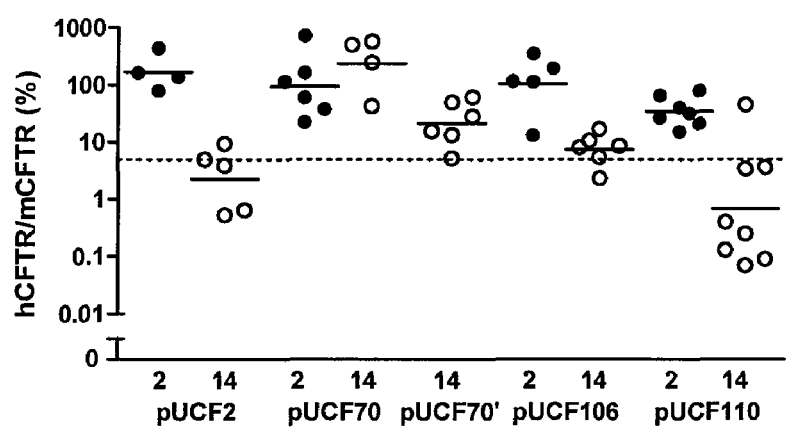
FIG. 8. Evaluation of whether active transcription of the inverted 3' BGH transcribed sequence is required for prolonged CO-CFTR mRNA expression. FABP mice were dosed IT with compacted pUCF106 (105 µg) or pUCF110 (102 µg) and animal lungs were harvested at days 2 and 14 for qRT-PCR analysis. Prior data in FABP mice dosed IT with pUCF2, pUCF70, and second pUCF70' study results are presented for comparison. (Solid lines indicate geometric means; dotted line equals 5%.)
Figure 16:
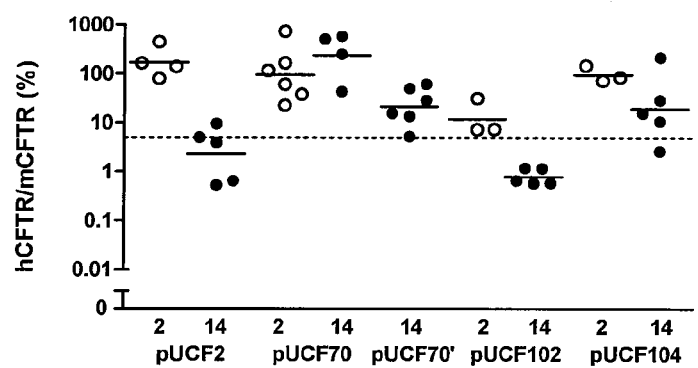
FIG. 16. Evaluation of inverted 3' BGH transcribed sequence subdomains. Male FABP mice were dosed IT with compacted pUCF102 (98 µg) or pUCF104 (105 µg) and animal lungs were harvested at days 2 and 14 for qRT-PCR analysis. For comparison are prior data in male FABP mice dosed IT with pUCF2, pUCF70, and pUCF70'. Dotted line equals 5%.

To evaluate if active transcription of the inverted 3' BGH transcribed sequence is necessary for its ability to generate prolonged CO-CFTR mRNA expression in the mouse lung, two plasmids were prepared that place a correctly oriented SV40 pA site either upstream (pUCF106) or downstream (pUCF110) of the inverted 3' BGH transcribed sequence in pUCF70.

pUCF106 generated a geometric mean CO-CFTR/mCFTR ratio of 102% at day 2 and 7.38% at day 14 (p=0.0015, t test of log-transformed data) (FIG. 8). This significant reduction in CO-CFTR mRNA expression indicates that active transcription of the inverted 3' BGH transcribed sequence is required for its ability to generate prolonged expression. However, a similar result was observed for pUCF110, which generated a geometric mean CO-CFTR/mCFTR ratio of 34.2% on day 2, which fell to 0.68% on day 14 (p=0.0016, t test of log-transformed data) (FIG. 8). Note that this t test was performed using the Welch's correction since the variances of the log-transformed data were not equal (F test). Initial results of a deletion analysis (see Examples 12 and 13, FIGS. 16-18) reveal that the region responsible for prolonged expression is located in a 3' domain of the inverted 3' BGH transcribed sequence. Theoretically, pUCF110 transient expression may be explained by the influence of adjacent SV40 pA sequences on the function of the inverted 3' BGH transcribed sequence, although this point needs further investigation.

To more easily evaluate this pUCF70 derivative analysis, the geometric means of the day 2 and day 14 hCFTR/mCFTR mRNA ratios, day 14/day 2 percentages, and t test comparisons for each plasmid are summarized in Table 2. Non-significant differences indicate maintained expression (unshaded cells).

TABLE 2

Gene expression comparisons for pUCF70-derivative vectors dosed in FABP (and FVB/N) mice.

| plasmid | description | day 2□ (%) | day 14□ (%) | day 14/day 2 (%) | p-value‡ |
|---|---|---|---|---|---|
| pUCF2 | older vector, no inverted BGH 3' | 167.2 | 2.289 | 1.37 | 0.0006 |
| pUCF70 | inverted BGH 3', flanking S/MARs | 94.08 | 235.5 | 250 | 0.2779 |
| pUCF90 | 'correctly' oriented BGH pA | 26.54 | 0.3785 | 1.43 | 0.0006 |
| pUCF92 | removal of BGH pA | 25.46 | 1.190 | 4.67 | 0.0007 |
| pUCF98 | removal of β-globin S/MAR | 104.3 | 15.64 | 15.0 | 0.0588 |
| pUCF88 | removal of INF-β S/MAR | 79.88 | 20.56 | 25.7 | 0.2629 |
| pUCF96 | hβ-actin promoter | 397.8 | 39.51 | 9.93 | 0.0653 |
| pUCF94 | SV40 promoter | 33.0 | 33.6 | 102 | 0.9858 |
| pUCF112 FVB/N | CMV promoter (in FVB/N) | 35.76 | 0.7208 | 2.0 | <0.0001 |
| pUCF80 | prokaryotic kanR backbone | 36.8 | 14.5 | 39.4 | 0.2052 |
| pUCF100 | removal of both S/MARs | 51.2 | 4.99 | 9.7 | 0.0007 |
| pUCF108 FVB/N | removal of both S/MARs + kanR | 4.19 | 4.84 | 116 | 0.8096 |
| pUCF108 | removal of both S/MARs + kanR | 19.46 | 8.997 | 46.2 | 0.2496 |
| PUCF106 | SV40 pA 5' to inverted BGH 3' | 102 | 7.38 | 7.2 | 0.0015 |
| pUCF110 | SV40 pA 3' to inverted BGH 3' | 34.2% | 0.68% | 1.99 | 0.0016 |

□geometric mean of hCFTR/mCFTR ratio
‡unpaired t test of log transformed day 2 and day 14 data; threshold significance is p = 0.05.

EXAMPLE 5

Discussion

Gene therapy requires the ability to achieve transgene expression at therapeutic levels in vivo, and for many indications, long-term expression is desired. Some non-viral episomal vectors have lower toxicities than viral vectors, but are prone to silencing [14, 15, 18]. In this application, different strategies were tested to improve episomal vector expression longevity and expression levels when delivered as compacted DNA nanoparticles [7].

One focus of this application is to optimize a hCFTR expression vector for therapy of the lungs of CF patients. In the first optimization step a firefly luciferase transgene and CpG-depleted plasmid elements were employed. Surprisingly, a completely CpG-depleted vector (pEEL) containing the luciferase gene driven by the EF1α promoter failed to produce prolonged expression in the mouse airway. Contradictory to our results, other research groups have demonstrated persistent luciferase activity in the mouse lung using a very similar CpG-depleted episomal vector [16]. The different outcome of these two experiments might be related to the pDNA delivery methods. The CK30PEG10K compacted DNA nanoparticle enters the cell and traffics to the nucleus via a non-degradative nucleolin mediated pathway [4], while lipid/DNA complexes enter the cell through clathrin-coated vesicle-mediated endocytosis or caveolar entry [24]. The CpG-enriched lipid/DNA complexes have been shown to stimulate toll-like receptor 9 (TLR9) innate immune responses in the lung, with induction of bronchoalveolar lavage fluid INF-γ, TNF-α, and IL-12 [25]. This TLR9 activation step may be responsible, in part, for decreased duration of transgene expression [16]. In contrast, CK30PEG10K compacted DNA nanoparticles (containing numerous CpGs in the plasmid payload) do not stimulate production of these BAL cytokines and do not appear to activate TLR9 [7]. However, the different trafficking pathway for plasmids delivered as nanoparticles appears to trigger a different silencing mechanism. So, CpG depletion may not improve expression longevity for CK30PEG10K compacted DNA. Nevertheless, pEEL-mediated transient luciferase activity levels were about 10-fold higher compared to CpG-enriched plasmids (data not shown) suggesting that CpG reduction or depletion may improve overall expression levels.

Our prior work and studies reported by other investigators have shown that some luciferase vectors containing the UbC promoter are able to generate prolonged activity in vivo [8, 18]. These data suggested that exchange of the EF1α promoter with UbC in the pEEL construct might be a useful strategy. pUL, a pEEL derivative containing multiple CpGs in the UbC promoter-exon1-intron region, demonstrated maintaining luciferase activity at levels comparable to pEEL transient expression. From these experiments we concluded that complete CpG depletion of the plasmid is not necessary to achieve persistent expression of the transgene, however partial or complete CpG depletion may possibly improve initial expression levels. These data are consistent with transgene expression in liver investigated by other researchers [26]. Motivated by these findings, we further improved the hCFTR expression cassette by creating a synthetic codon optimized and almost CpG-depleted (1 CpG) hCFTR synthetic sequence, CO-CFTR. The natural hCFTR cDNA and synthetic CO-CFTR were subcloned into the pUL vector in place of luciferase (pUCF and pUCF2, respectively) and tested in HEK293 cells for protein expression. pUCF2 was more efficient and produced 9-fold more hCFTR protein compared to pUCF.

To measure hCFTR mRNA and compare it with mCFTR mRNA in the mouse lung, a validated qRT-PCR assay was developed that allows precise comparison of target expression regardless of differences in amplification efficiency of separate targets. This assay was tested using special validation vectors containing both target sequences and proved to be suitable for hCFTR expression analysis. This approach was used in animal experiments to measure CO-CFTR expression relative to endogenous mCFTR (CO-CFTR/mCFTR×100%).

Unfortunately, neither pUCF nor pUCF2 maintained transgene expression in dosed animals and fell below 1% at day 14. Of note, the transient expression (at day 2) for pUCF2 was 14.6-fold higher than for pUCF. These mRNA and protein findings strongly suggest that CO-CFTR is transcribed and/or processed and translated more efficiently than natural CFTR cDNA in the context of these vectors.

We hypothesized that human CFTR protein may cause an immunogenic reaction in transfected mice followed by either transcriptional silencing or loss of cells producing the transgene. To test this hypothesis, compacted pUCF2 DNA was dosed in immunodeficient SCID mice and FABP mice (which express human CFTR protein in the gut). The "immunogenic response" hypothesis was dismissed because CO-CFTR expression was not persistent in SCID or FABP mice. However, transient CO-CFTR expression in FABP mice was higher than in Balb/c mice. An evaluation of parental strains that comprise FABP mice, 129, C57, and FVB/N mice, did not reveal high mRNA levels of CO-CFTR on day 2. The improved hCFTR expression at day 2 in FABP mice could be due to several factors, including increased gene transfer efficiency, improved activity of the vector expression cassette, and improved hCFTR mRNA processing and/or nuclear export. It is conceivable that one or more of these potential factors might be related to expression of endogenous mutant mCFTR (truncated at codon 489). For example, production of cell surface nucleolin, which is responsible for compacted DNA cellular uptake (and facilitates cytoplasmic transport and nuclear uptake), might be upregulated as a consequence of CFTR mutations. Although CFTR protein is known to affect various endocytosis and exoctyosis pathways [27, 28], there are no prior reports evaluating nucleolin expression levels or rates of cell membrane presentation.

Multiple pUCF2 derivatives were screened in vivo for their ability to maintain persistent CO-CFTR expression. Surprisingly, one pUCF2 derivative, pUCF70, which contains an inverted 3' BGH transcribed sequence, was able to maintain CO-CFTR mRNA expression above the 5% threshold level for at least 59 days. A detailed analysis of mRNA generated by pUCF70 revealed that the CO-CFTR transcript has a 3'UTR that includes the inverted 3' BGH transcribed sequence, the interferon-β S/MAR, the bacterial ZeoR expression cassette, the R6K origin, and part of the β-globin S/MAR sequence. For pUCF70, the finding that the CO-CFTR transcript terminates in the β-globin S/MAR suggested several mechanisms that may partially explain the observed improved persistence of CO-CFTR mRNA in FABP mice. S/MAR domains have multiple properties, including attachment to the nuclear matrix at sites that appear favorable for mRNA transcription and processing [29]. Although there are not sequence specific areas of homology between various S/MAR domains, they do share one property—they have regions that respond to negative helical stress by unwinding activity [30, 31]. We postulated that active transcription through the INF-β S/MAR and/or through much of the β-globin S/MAR may establish plasmid replication or improve S/MAR function, thereby improving efficiency of episomal nuclear plasmid localization to nuclear matrix zones of active transcription and post-transcriptional processing (splicing and nuclear export). In some way, favorable nuclear location of pUCF70 might diminish probabilities of transcriptional silencing, perhaps by inhibiting heterochromatin formation. Of note, pUCF70 and its derivative lacking a 3' BGH transcribed sequence (pUCF92) were not able to replicate extrachromosomally in tissue culture. Moreover, pUCF70 derivatives lacking one (pUCF88 and pUCF98) or both S/MARs (pUCF 108) were able to maintain CO-CFTR expression in vivo. In contrast, a pUCF70 derivative (pUCF90) containing both S/MARs but lacking the inverted 3' BGH transcribed sequence (pUCF92) was silenced. These results suggest that S/MAR sequences are not absolutely necessary for prolonged expression while presence of the inverted 3' BGH transcribed sequence is critical.

We initially hypothesized that transcription of the prokaryotic cassette as a 3'UTR in the CO-CFTR transcript may be important in diminishing probabilities of heteochromatin formation in pUCF70 DNA. Improved duration of expression by minicircles compared to plasmids in the liver may relate to removal of DNA domains that are prone to nucleosome formation, with subsequent heterochromatin encroachment into the eukaryotic transcriptional cassette resulting in transgene silencing [32]. Active transcription of the prokaryotic domain in pUCF70 may, in a similar fashion, diminish nucleosome formation. It is noteworthy, however, that evaluation of CO-CFTR minicircles and linear fragments in the Balb/c lung were not successful in generating prolonged CO-CFTR expression (data not shown). Moreover, active transcription of the ZeoR prokaryotic cassette in plasmid pUCF 100, which contains the inverted 3' BGH transcribed sequence but no S/MARs, was unsuccessful in generating persistence CO- CFTR expression. These findings suggest that active transcription of the prokaryotic cassette in the mouse lung may not have a significant role in facilitating prolonged transgene expression.

To evaluate if active transcription of the inverted 3' BGH transcribed sequence is necessary for its ability to generate prolonged CO-CFTR mRNA expression in the mouse lung, the pUCF106 plasmid was prepared that places a correctly oriented SV40 pA site upstream of the inverted 3' BGH transcribed sequence in pUCF70. The pUCF106 plasmid was silenced, confirming the necessity of transcription of the inverted 3' BGH transcribed sequence for persistent CO-CFTR expression.

To further evaluate if transcription of an S/MAR domain facilitates prolonged expression, vectors pUCF100 and pUCF110 were created and tested in FABP mice. In pUCF100 both S/MARs were removed. pUCF110 contains both S/MARs but their transcription was prevented by inserting an SV40 pA between the inverted 3' BGH transcribed sequence and first S/MAR domain. In both cases only transient expression was observed. It is tempting to conclude that in addition to the inverted 3' BGH transcribed sequence, transcription of an S/MAR domain as a 3' UTR is required for prolonged CO-CFTR mRNA expression. However, prolonged CO-CFTR expression by pUCF108, which has no S/MARs and a different prokaryotic cassette than pUCF100, suggest a different possibility. Theoretically, sequences adjacent to the inverted 3' BGH transcribed sequence may influence formation of secondary structure and modify its function. This scenario might explain failure of persistence in pUCF100, which has an R6K origin adjacent to the inverted 3' BGH transcribed sequence, whereas pUCF108 demonstrates persistence and has an MB1 origin adjacent to the inverted 3' BGH transcribed sequence. This hypothesis remains to be tested, although studies in progress are designed to explore the possibility that secondary structure of the inverted 3' BGH transcribed sequence in the 3' UTR of CO-CFTR mRNA plays a significant role in expression persistence.

CO-CFTR expression in pUCF70 was driven by the UbC promoter. To determine if the UbC promoter is necessary for pUCF70 derivatives to produce prolonged CO-CFTR mRNA expression, pUCF96 (with human β-actin promoter), pUCF94 (with SV40 early promoter), and pUCF 112 (with CMV promoter) were tested in the FABP and FVB/N lungs. Two of three tested plasmids (containing SV40 or human β-actin promoters) achieved maintained expression at day 14, indicating that the UbC promoter is not absolutely necessary to maintain CO-CFTR expression. In contrast, the CMV promoter containing construct (pUCF112) was silenced. This result is perhaps not surprising, since the CMV promoter has been reported to be silenced in multiple systems and numerous mechanisms have been implicated for silencing [7, 18, 33, 34].

In our previous studies (data not shown), we found that KanR and Col EI containing prokaryotic backbones have strong silencing effects on the luciferase transgene, but expression can be maintained by insulating the prokaryotic cassette with flanking INF-β and β-globin S/MAR sequences, or pairs of chicken HS4 insulators [35]. Since, KanR containing backbones are typically employed in human clinical trials, we tested KanR in pUCF70 derivatives (pUCF80 and pUCF108). Both plasmids contained the same CpG-rich KanR-MB 1 backbone, and in pUCF80 this backbone was insulated with flanking INF-β and β-globin S/MAR sequences. Surprisingly, both plasmids maintained CO-CFTR expression at least for 30 days, although CO-CFTR/mCFTR geometric mean ratios were lower at each time point compared to pUCF70. Undiminished CO-CFTR mRNA expression by pUCF70 in FABP mice out to day 59 further highlights the favorable features of this plasmid.

In summary, we identified a new genetic element, the inverted 3' BGH transcribed sequence, that allows maintenance of CO-CFTR expression using many different vectors. This element is successful in facilitating prolonged CO-CFTR mRNA expression in plasmids containing either the CpG-depleted ZeoR-R6K backbone or the CpG-enriched KanR-MB1 backbone, and promoters other than UbC can be employed. The mechanism by which the inverted 3' BGH transcribed sequence facilitates prolonged CO-CFTR mRNA expression remains undefined and will require further investigation. Our studies indicate that the inverted 3' BGH transcribed sequence must be transcribed in order to facilitate maintained expression; it appears non-functional when present in the plasmid as a non-transcribed element. These findings highlight the possibility that the inverted 3' BGH transcribed sequence may bind other transcriptional control factors as an mRNA structural element. Deletion analysis and gel-shift assays using nuclear extracts may provide more insight about mechanisms underlying the inverted 3' BGH transcribed sequence. Regardless of the mechanism(s) involved, we have shown that plasmids can be developed that provide clinically-relevant levels of hCFTR mRNA expression for prolonged duration in the mouse lung.

EXAMPLE 6

Materials and Methods
DNA Vector Construction

DNA vectors were constructed using standard molecular biology techniques [36]. Each DNA fragment that was amplified by PCR or synthesized or obtained from a third party was sequenced. All DNA junction regions were sequenced. Plasmid integrity was confirmed by restriction analysis using at least four restriction endonucleases.

pEEL is a derivative of the CpG-depleted commercial vector pCpG-mcs (Invivogen). The CpG-depleted luciferase gene ORF was amplified from the plasmid pModLucSh (Invivogen) using 5'ATACACCATGGAGGATGCCAAGAATAT-TAAG (SEQ ID NO: 6) and 5'ATACAACTAGTCTAGAT-TATTTG-CCACCCTTCTTGGCCT (SEQ ID NO: 7) primers. The stop codon (TAA) and two restriction sites (XbaI and SpeI) were added to the 3' end during amplification. The obtained PCR fragment was digested with NcoI and SpeI and subcloned into the pCpG-mcs/NcoI/NheI vector.

pUL. The hEF1-α promoter and synthetic intron were deleted from pEEL using SpeI and NcoI. The UbC promoter, first exon and intron sequence were amplified from the pUb-Lux plasmid [18] (kindly provided by Deborah Gill, University of Oxford, UK) using 5'ACATATCTAGA-CTGCAGGC-CTCCGCGCCGGGTTTTG (SEQ ID NO: 8) and 5'GTCTTCCATGGTGGCTAGCTCGTCTAACA (SEQ ID NO: 9) primers. Additional XbaI, PstI and Nco I sites were added during amplification. The PCR fragment was digested with XbaI and NcoI and subcloned into the pEEL/SpeI/NcoI vector. The mCMV enhancer was deleted from the obtained vector using PstI.

pUCF. The luciferase gene was deleted from pUL by digesting with Nhe I and Xba I. The obtained vector was blunted using Klenow fragment and dephosphorylated. The hCFTR sequence was cut from pKCPIRCFTRBGH (−) [9] using Kpn I and Apa I. The obtained hCFTR encoding DNA fragment was blunted using T4 DNA polymerase and ligated into the pUL/Nhe I/Xba I blunted vector.

pUCF2. The luciferase gene was deleted from pUL by digesting with Nhe I and Xba I, followed by dephosphorylation with CIP. The codon optimized, CpG-depleted (only 1 CpG) hCFTR gene was synthesized by GenScript and subcloned into the pUC57 plasmid. The synthetic hCFTR (CO-CFTR) was cut from pUC57 hCFTR using Nhe I and Xba I. The obtained hCFTR fragment was ligated into the pUL/Nhe I/Xba/CIP vector.

pUCF70 is a derivative of pUCF2. The BGH pA extended sequence (712 bp) was amplified from the RYO2 plasmid (kindly provided by Richard Hanson, Case Western Reserve University, OH) with 5'ATATCTCTAGAAATTCTAT-GATTTCTATCATTACTTC (SEQ ID NO: 10) and 5'GTGAACATATTGACTC-AATTGGGCTGGGCAGATC-CTCA (SEQ ID NO: 11) primers. The partial IFN-β S/MAR sequence was amplified from pUL using 5'TGAGGATCT-GCCCAGCCCAATTGAGTCAATATGTTCAC (SEQ ID NO: 12) and 5'TATGGTATGAC-ATATGGGTTCCCTTT-TATT (SEQ ID NO: 13) primers. The PCR fragments were joined by a "bridge" PCR. The obtained DNA fragment was digested with Sac I and Xba I followed by ligation into the pUCF2/Xba I/Sac I/CIP vector.

pUCF90. pUCF70 was digested with Xba I and Mfe I. The obtained fragments were blunted with Klenow fragment and ligated back. The clone with the correct BGH pA orientation was selected.

pUCF92. pUCF70 was digested with Xba I and Mfe I to delete the BGH pA sequence. The 7650 by fragment was isolated, blunted with Klenow fragment and self-ligated.

pUCF96. A region containing the human β-actin promoter was amplified from human genomic DNA, "bridged" with the R6K-βGlobin S/MAR region, and digested with Ase I and Nhe I. The obtained fragment was subcloned into the pUCF70/Ase I/Nhe I/CIP vector.

pUCF106. The fragment containing the SV40 pA sequence was amplified from pUL using 5'ACATAACTAGT-GCTAGCCAGACATGATAAGATACATTG (SEQ ID NO: 14) and 5'GAATTTCTAGACC-ATACCACATTTGTAGAG-GTTTTAC (SEQ ID NO: 15) primers. The PCR fragment was digested with Spe I and Xba I and subcloned into the pUCF70/Xba I/CIP vector.

pUCF112. The CMV enhancer-promoter-exon-intron fragment was cut from pKCPIRCFTRBGH(−) [9] with Avr II, blunted with Klenow fragment and digested with Spe I. The obtained fragment was subcloned into the pUCF94/Bam HI (blunted with Klenow)/Nhe I/CIP vector.

pUCF80. The Kan R gene driven by the EM7 promoter and the MB1 origin of replication were amplified from the psiRNA-hH1NeoG2 plasmid (Invivogen) using 5'CTTGAC-GAGTTCTTCTGACATGTGAGCAAAAGGCCAGCA (SEQ ID NO: 16) and 5'GATATCATGACCAA-AATCCCT-TAACGTGAGTTTTC(SEQ ID NO: 17), and 5'TGCTGGC-CTTTTGCTCACATGTCAGAAGAACT-CGTCAAG (SEQ ID NO: 18) and 5'ACAATTAATTAATTGACAATTAAT-CATCGGCATAGTA (SEQ ID NO: 19) primer sets, correspondingly. The obtained DNA fragments were joined by a "PCR bridge" reaction using 5'ACATATCTAGACAAT-TAATTAATTGACAATTAATCAT (SEQ ID NO: 20) and 5'TATTGTCTAGATATCATGA-CCAAAATCCCTTAACG (SEQ ID NO: 21) primers, digested with Xba I, and self-ligated. The obtained pNeo plasmid had very low yields, indicating a negative interaction between the MB1 on and the Kan R gene. To improve plasmid yield, the MB1 ori was inverted by digesting pNeo with Eco RV and Pci I, blunting with T4 DNA polymerase, and ligating back (pNeo2). To make a polylinker, the 5'CTAGCAAGCTTAATTAAG-GATCCat (SEQ ID NO: 22) and 5'GGATCCTTAAT-TAAGCTTg (SEQ ID NO: 23) oligonucleotides were annealed and ligated into the pNeo/Pac I vector, producing pNeo3. A fragment containing CO-CFTR expression cassettes flanked by S/MARs was cut from pUCF70 with Pac I and subcloned into the pNeo3/Pac I/CIP vector to create the pUCF80 construct.

pUCF108. The SV40 pA sequence was amplified from pUL using 5'TTAATGGATCCAGACATGATAAGATA-CATTGATG (SEQ ID NO: 24) and 5'TGCAGGAATTC-CATA-CCACATTTGTAGAGGTTTTAC (SEQ ID NO: 25) primers. The PCR fragment was digested with Bam HI and Eco RI and subcloned into the pUCF80/Bam H I/Eco RI/CIP vector. The obtained plasmid (pUCF86) was cut with Pac I, blunted with T4 DNA polymerase, purified, digested with Xba I, and dephosphorylated with CIP. The DNA fragment encoding the BGH pA sequence was isolated from pUCF70 by cutting with Mfe I, blunting with Klenow fragment, purifying, and subsequently cutting with Xba I. The obtained BGHpA/Mfe I (blunted with Klenow)/Xba I fragment was subcloned into the pUCF86/Pac I(blunted with T4 DNA polymerase)/Mfe I/CIP vector.

pUCF88. To remove the IFN-β S/MAR sequence, the region containing the ZeoR expression cassette and partial R6K on sequence was amplified from pUCF70 with 5'GATATCTCTAGATTGACAATTAAACAT-TGGCATAGTA (SEQ ID NO: 26) and 5'AAGGTTTTAAG-GTTTC-CTAGGTTATCCTCAGTC (SEQ ID NO: 27) primers. The PCR fragment was digested with Xba I and subcloned into the pUCF70/XbaI/Dra I/CIP vector. The obtained plasmid (pUCF76) was linearized by Xba I and ligated into the BGH encoding fragment, which was isolated from pUCF90 by digestion with Xba I.

pUCF42. The S/MAR regions were deleted from pUL vector by digestion with Pac I and Eco RI enzymes. A fragment containing the R6K-ZeoR region was blunted with T4 DNA polymerase and ligated with a luciferase expression cassette containing fragment that was blunted with Klenow (pUL3). R6K ori and Zeo R expression cassettes were amplified from the pUL3 template using 5'TCTGACGTG-GCAGCGCTCGCCGTGA (SEQ ID NO: 28) and 5'ACATATCTAGAATTCAAGATCAGCAGTT-CAACCTG (SEQ ID NO: 29) primers. The obtained DNA fragment was digested with Pst I and Xba I enzymes and ligated with a pUL3/Pst I/Xba I fragment containing the Luc expression cassette lacking an SV40 pA region (pUL3del_pA). The SV40 pA was amplified from pUL3 template using 5'AAT-TAATGCATCCAGACATGATAAGATACATTGATG (SEQ ID NO: 30) and 5'TTAATATGCATCCATACC-ACATTTG-TAGAGGTTTTAC (SEQ ID NO: 31) primers. The obtained fragment was digested with Nsi I enzyme and subcloned into pUL3del_pA/Pst I/CIP vector (pUL9). A completely CpG-depleted CO-CFTR gene was excised with Nhe I and Xba I enzymes from pUCF22 vector (pUCF22 is derivative of pUCF2 that contains completely CpG-depleted CO-CFTR gene). The obtained fragment was subcloned into the pUL9/Nhe I/Xba I/CIP vector.

pUCF98. The IFN-β S/MAR was amplified from pUL plasmid with 5'ATATCTCTAGAGAGTCAATATGTTCAC-CCCAAAAAAGC (SEQ ID NO: 32) and 5'TGATATCTA-GAGGAT-CCACAGATGTTACTTAGCCTTTTA (SEQ ID NO: 33) primers. The PCR fragment was digested with Xba I enzyme and subcloned into pUCF42/XbaI/CIP vector (pUCF74). The CO-CFTR expression cassette with adjacent regions was cut from pUCF70 using Sac I and Sac II. The obtained fragment was subcloned into the pUCF74/Sac I/Sac II/CIP vector.

pUCF94. The early SV40 promoter was amplified from the pRC-RSV plasmid (Invitrogen) using 5'TTCCTGCAG-GATCCAGGCAGGCAGAAGTATGCAAAG (SEQ ID NO: 34) and 5'CGGCTGCGACGGAACTC-GAAAATG-GATATCCAAGCTC (SEQ ID NO: 35) primers. The Ub_exon1-intron fragment was amplified using 5'GAGCT-TGGATATCCATTTTCGagttccgtcgcagccgg (SEQ ID NO: 36) and 5'CTTGGCATCCTCCATGGtggc-tagctcgtc (SEQ ID NO: 37) primers. The PCR fragments were joined using a "bridge PCR". The "bridged" fragment was digested with Pst I and Nhe I and subcloned into the pUL/Pst I/Nhe I/CIP vector (producing pSVL). The fragment containing the SV40 promoter was cut from the pSVL plasmid with Nhe I and Ase I, and subcloned into the pUCF70/Nhe I/Ase I/CIP vector.

pUCF100. The BGH pA sequence was cut from pUCF70 with Xba I and Mfe I. The obtained fragment was subcloned into the pUCF98/Eco RI/Xba I vector.

pUCF110. The SV40 pA sequence was amplified from pUL with 5'ATACACAATTGCCAGACATGATAAGATA-CATTGA (SEQ ID NO: 38) and 5'AGAAACAATTGAAT-TCCATA-CCACATTTGTAGAG (SEQ ID NO: 39) primers. The obtained DNA fragment was digested with Eco RI and subcloned into the pUCF70/MfeI/CIP vector.

pUCF102. Deletion of "A" region was performed by amplification of fragment containing "B" and "C" (consisting of "D" and "E") regions from pUCF70 with 5'ATATCTCTA-GATTGAAGGCGGAGCCCTCCTGAGCTA (SEQ ID NO:53) and 5'GTGAACATATTGACTCAAT-TGGGCTGGGCAGATCCTCA (SEQ ID NO:54) primers, digestion of this fragment Xba I and Mfe I enzymes, and ligation with pUCF70/Xba I/MfeI/CIP vector.

pUCF104. Deletion of "A" and "B" regions was performed by amplification of "C" region (consisting of "D" and "E") regions from pUCF70 with 5'ATATCTCTAGAAGTGG-GAGTGGCACCTTCCAGGGTC (SEQ ID NO:55) and 5'GTGAACATATTGACTCAAT-TGGGCTGGGCAGATCCTCA (SEQ ID NO:54) primers, digestion of this fragment Xba I and Mfe I enzymes, and ligation with pUCF70/Xba I/MfeI/CIP vector.

pUCF114. Deletion of "E" region was obtained by digestion of pUCF104 plasmid with Bsm BI and Mfe I enzymes following by DNA end blunting with Klenow fragment, isolation of vector from gel and self-ligation.

pUCF116. Deletion of "D" region was obtained by digestion of pUCF104 plasmid with Xba I and Bsm BI enzymes following by DNA end blunting with Klenow fragment, isolation of vector from gel and self-ligation.

pUCF200. The luciferase gene was deleted from pUL by digesting with Nhe I and Xba I, followed by dephosphorylation with CIP. The "nucleosome non-friendly" NN5hCFTR gene was synthesized by GeneArt and subcloned into the pGA14 plasmid (0712900pGA14). The synthetic hCFTR (NN5hCFTR) was cut from 0712900pGA14 using Nhe I and Xba I. The obtained hCFTR fragment was ligated into the pUL/Nhe I/Xba/CIP vector.

Compacted DNA Preparation

Compacted DNA was manufactured by adding the DNA solution at a controlled rate to a vortexing tube of PEGylated polylysine (CK30PEG10k) [9]. CK30PEG10k and DNA were formulated at a final charge ratio of 2:1. This manufacturing was performed inside a laminar flow hood. The DNA working stock (20 ml, 0.1 mg/ml) was added to 2.0 ml of CK30PEG10k (3.2 mg/ml) stock at a rate of 4 ml/min by a syringe pump and through sterile tubing ended with a blunt cannula. During this addition, the tube of CK30PEG10k was vortexed at a controlled rate so that the two materials mixed instantaneously. Each batch consisted of about 22 ml of compacted DNA at a concentration of approximately 0.09 mg/ml. The compacted DNA was then filtered through a vacuum driven sterile filter with 0.2 µm polyethersulfone membrane.

The filtered sample of compacted DNA was then concentrated 20-30 fold using VIVASPIN centrifugal concentrators (MWCO 100k). The concentrated DNA was then diluted 20-30 fold with 0.9% NaCl to remove excess CK30PEG10k and exchange solvents with physiologic saline. Then the compacted DNA was concentrated again 20-30 fold, to a final concentration of 2-4 mg/ml. After formulation, the compacted DNA underwent several quality control tests, including sedimentation, turbidity, gel electrophoresis, transmission electron microscopy, and fluorescamine assays. These methods are described in [10]. Also, endotoxin levels were checked using an ENDOSAFE® PTS (Portable Test System) manufactured by Charles River Laboratories.

Intra-nasal (IN) and Intra-Tracheal (IT) Dosing in Mice

Each IN dosed mouse was given an intraperitoneal injection of 100-150 µl anesthetic cocktail (8.6 mg/ml ketamine, 0.29 mg/ml acepromazine, and 1.7 mg/ml xylazine). An EDP-Plus electronic pipette (Rainin) was programmed to deliver 10×2.5 µl aliquots, for a total of 25 µl of compacted DNA. The anesthetized mouse was hand-held, ventral side up. The bottom lip of the mouse was gently pushed up over the mouth, sealing the mouth shut. The electronic pipette was quickly placed on the bridge of the nose and 10 doses of 2.5 µl compacted DNA were given, for a total administered dose of 25 µl. The compacted DNA was at a concentration of 4 mg/ml in saline, for a total dose of ~100 µg per mouse. The doses were given at such a rate that the mouse inhaled the droplets before large droplets were allowed to accumulate on the nose. After administration, the mouse was immediately placed ventral-side down and allowed to recover. A heating blanket was used for 24 hours under the cage to aid in recovery and to prevent anesthesia-related hypothermia.

For IT dosing, each mouse was given an intraperitoneal injection of 100-150 µl of the anesthetic cocktail listed above. The mouse hair on the front of the neck was removed and betadine solution was applied to the area. Each mouse was situated on a surgical board at a 30% incline [10] and a tracheostomy was performed. A 50-µl aliquot of compacted DNA was administered as a bolus into the trachea using a manual pipette and 22-gauge catheter (Becton-Dickinson). For IT dosing, the compacted DNA was at a concentration of 2 mg/ml in saline, for a total dose of 100 µg per mouse. After the bolus was delivered, the wound was covered with betadine solution. The mouse was immediately placed ventral-side down and allowed to recover. A heating blanket was used for 24 hours under the cage to aid in recovery and to prevent anesthesia-related hypothermia.

Assays for Luciferase Activity and Protein Content

After sacrifice, lungs were perfused with PBS via the heart and then excised. Lungs were then frozen in 2-ml tubes on dry ice and stored at −80° C. until homogenization. Mouse lungs were allowed to thaw on wet ice. A 1-ml aliquot of 1× Cell Culture Lysis Reagent (Promega) and a 5 mm stainless steel bead (Qiagen) were added to each tube. The lungs were homogenized for 4 minutes at 30 Hz using a Qiagen TissueLyser. Tubes were again frozen on dry ice and then thawed for 5 minutes or less in a 37° C. water bath to further lyse the cells. Lysates were centrifuged at high speed at 4° C. for 5 minutes. Supernatants were collected and stored on wet ice when in use for assays, or stored at −65° C. to −80° C. for long-term storage. Using a Berthold Lumat LB9507 luminometer, a 100 ml aliquot of luciferin substrate (Promega) was added to 20 µl of each sample and luminescence was determined over 10 seconds. Each sample was read in duplicate. Relative light unit (RLU) values were normalized by protein values in the sample (RLU/mg protein). Protein values were determined by DC protein assay (BioRad). In order for protein values to fall within the standard curve, each lung lysate supernatant was diluted 5-fold with 1× Cell Culture Lysis Reagent prior to measurement.

Preparation of Total RNA and cDNA Synthesis

Mouse lungs harvested for RT-PCR were collected in 2 mL tubes containing a 5 mm stainless steel bead (Qiagen) and 1 mL of 1× Nucleic Acid Lysis Solution (Applied Biosystems). Samples were immediately placed on dry ice and kept at −80° C. Frozen lungs were thawed on wet ice for 30 min. before homogenization. Homogenization was performed using a TissueLyser for 4 min. at 30 Hz, a total of three times, cooling on ice for 5 min. between homogenizations. Dilution of the homogenate was made by adding 50 µL of homogenate to 750 µL of 1× Nucleic Acid Purification Lysis Solution (Applied Biosystems). Total RNA was isolated from the lungs using a 6100 Nucleic Acid PrepStation (Applied Biosystems) as recommended by the supplier. 300 µl of the diluted and filtered homogenate was used for the isolation. Total RNA was treated with Turbo DNA-free DNase (Ambion) to remove contaminating DNA (37° C. for 40 min).

The reverse transcription reaction was performed using the High Capacity cDNA RT Kit (Applied Biosystems) as recommended by the supplier. Minus RT reactions were set up, substituting nuclease-free water for Multiscribe Reverse Transcriptase in each reaction. All RT reactions were diluted 1:1 with nuclease-free water.

Real-time Quantitative TaqMan RT-PCR

Quantitative RT-PCR assays were performed using the ABI Prism 7300 Real Time PCR System and Sequence Detection V1.3.1 software (Applied Biosystems). Fluorogenic probe and oligonucleotide primer combinations for TaqMan assays were designed using Primer Express V3.0 (Applied Biosystems). The TaqMan CO-CFTR RT-PCR primer set K6, forward (5'TGTGCTGAGCAAGGCCAAG; SEQ ID NO: 40), reverse (5'CAGGGTTCTTCTGATGATCTGGTAG; SEQ ID NO: 41) and Fam/Tamra probe K (5'-FAM CTCTGCCCACCTGGACCCTGTGA; SEQ ID NO: 42) were specific to CO-CFTR mRNA. The TaqMan mCFTR RT-PCR assay primer set B8 forward primer (5'CTAGTCCATTCCCAGAACCCAT; SEQ ID NO: 43), reverse (5'GGGATCCACCTGTCTCTGTGTC; SEQ ID NO: 44), and Fam/Tamra probe B (5'-FAM AGGCATTTCCCATGCTTCTAACCCCA; SEQ ID NO: 45) detected endogenous mouse CFTR mRNA. The TaqMan mGAPH RT-PCR primer set A forward primer (5'TGGCCTCCAAGGAGTAAGAAAC; SEQ ID NO: 46), reverse primer (5'GGGATAGGGCCTCTCTTGCT; SEQ ID NO: 47), and Fam/Tamra probe A (5'-FAM ACCACCCACCCCAGCAAGGACAC; SEQ ID NO: 48) detected mouse GAPDH, which was used as a normalizer. The TaqMan luciferase RT-PCR forward primer, T10, (5'CTCCACTGGACTGCCCAAAG; SEQ ID NO: 49), reverse primer, T10 (5'GCAGTGTCAGGGATGATCTCCT; SEQ ID NO: 50), and Fam/Tamra probe T (5'-FAM GATTGAGCCATGCCAGAGACCC; SEQ ID NO: 51) were used to detect luciferase mRNA. The relative quantitation mode was used in all RT-PCR assays, which contained 900 nM of forward primer, 900 nM of reverse primer, and 250 nM probe in a total volume of 25 of which 5 µl was cDNA. All samples were assayed in quadruplicate, including the minus RT reactions. Rarely contamination was detected, but ignored because the difference between plus and minus RT signals was more than 6 Cts.

IP/Western Analysis

HEK293 cells were plated onto 60 mm dishes and transfected with either 0.75 µg or 3 µg of plasmid using Lipofectamine reagent (InVitrogen). Cells were collected on day 2 post transfection and lysed in Buffer A (50 mM Tris, pH 7.4, 150 mM NaCl, 1 mM EDTA) including 1% Triton X 100 and protease inhibitors (Roche Complete Mini Protease Inhibitor Tablets) for 30 minutes on ice. The lysate was centrifuged at 16,000×g for 5 minutes at 4° C. and the resulting supernatant was stored at −80° C. until further analysis. Rec-Protein G sepharose 4B (Zymed) was incubated with the immunoprecipitating anti-CFTR antibody (R&D Systems) overnight at 4° C. while rocking. The resin-antibody complexes were washed with Buffer A including 0.1% Triton X 100, and incubated with the transfected cell culture supernatant overnight at 4° C. while rocking. The complexes were collected by pulse centrifugation and washed with Buffer A including 0.1% Triton X 100 and protease inhibitors. The complexes were resuspended in 2× sample loading buffer and incubated at 95° C. for 5 minutes. The sample supernatants were run on a 4-20% SDS Tris-glycine gel (InVitrogen) and transferred to Protran nitrocellulose paper (Whatman) using the Multiphor II Transfer System (Pharmacia). The nitrocellulose blot was washed briefly in TBS (Sigma) and blocked in SuperBlock T-20 (Thermo Scientific). The blot was incubated with the mouse monoclonal anti-CFTR antibody (R&D Systems #MAB1660) followed by ECL anti-mouse IgG HRP (GE Healthcare/Amersham #NA391V). HRP detection was through the SuperSignal West Femto Maximum Sensitivity Substrate Kit (Thermo Scientific) and the blot was exposed to the Fluor S Multi Imager (Bio-Rad) for 5 minutes.

Northern Blotting Analysis

HEK293 cells were plated onto 100 mm dishes and transfected with 8µg of plasmid using Lipofectamine reagent (InVitrogen). Cells were collected on day 2 post transfection and total RNA was isolated using the RNeasy Mini Kit (Qiagen). The mRNA was isolated from total RNA using the Oligotex mRNA Mini Kit (Qiagen). For electrophoresis, mRNA samples were prepared in NorthernMax-Gly Sample Loading Dye (Ambion), heated to 50° C. for 30 minutes, and run on a 1% agarose gel prepared in NorthernMax-Gly 10× Gel Prep/Running Buffer (Ambion). The gel was transferred to Nytran SuperCharge nylon membrane (Whatman) in 5×SSC/10 mM NaOH using the Turboblotter Rapid Downward Transfer System (Whatman) for 2 hours. The blot was rinsed briefly in 5×SSC (InVitrogen) and baked for 30 minutes at 80° C. Probe labeling and hybridization utilized the ECL Direct Nucleic Acid Labeling System (Amersham). After hybridization overnight at 42° C., the blot was washed twice in 0.5×SSC/0.4% SDS for 10 minutes at 50° C. followed by twice in 2×SSC for 10 minutes at room temperature. Detection of the bands of interest was through the SuperSignal West Femto Maximum Sensitivity Substrate Kit (Thermo Scientific) and exposure to the Fluor S Multi Imager (Bio-Rad) for 5 minutes.

Plasmid Replication Assay

HeLa cells were plated onto 60 mm dishes and transfected with 8µg of plasmid using Lipofectamine 2000 reagent (InVitrogen). Cells were collected on day 4 post transfection and genomic DNA was isolated using the Blood & Cell Culture DNA mini Kit (Qiagen). An aliquot of 10 µg DNA was digested simultaneously with NheI (Fermentas) and DpnI (New England BioLabs) and an aliquot of 0.5 µg DNA was digested with NheI alone. All the digests were performed overnight at 37° C. The larger digests were mixed with five volumes of PB buffer (Qiagen) and the DNA was purified using the QIAquick Gel Extraction Kit (Qiagen). The digests were run on a 0.7% agarose/0.5×TAE (InVitrogen) gel at 80 volts for approximately 2 hours. Following electrophoresis, the gel was exposed to UV light for 4 minutes, and treated with denaturing buffer [36] (2×15 minutes), neutralization buffer (2×15 minutes), 10×SSC (InVitrogen) buffer (2×10 minutes), and transferred in 10×SSC using the Turboblotter Rapid Downward Transfer System (Whatman) for 3 hours. The blot was briefly rinsed in 2×SSC and baked at 80° C. for 15 minutes. Probe labeling and hybridization utilized the ECL Direct Nucleic Acid Labeling System (Amersham). After hybridization overnight at 42° C., the blot was washed twice in 1×SSC/0.4 SDS for 10 minutes at 50° C. followed by twice in 2×SSC for 10 minutes at room temperature. Detection of the bands of interest was through the SuperSignal West Femto Maximum Sensitivity Substrate Kit (Thermo Scientific) and exposure to the Fluor S Multi Imager (Bio-Rad) for 5 minutes.

Statistical Analysis

For analysis and for presentation in Figures and Tables, luciferase activity data (RLU/mg protein/µg DNA), mRNA data (hCFTR or CO-CFTR/mCFTR), and DNA data (vector DNA/mCFTR genomic DNA) were log-transformed in order to equalize variances and make distribution of data points more Gaussian. Consequently, comparisons are made between geometric means of the data and 95% CI and SEM are shown on a logarithmic scale. Ratios of mCFTR mRNA to mGAPDH mRNA in various mouse strains were not log-transformed since in all cases but one the data conformed to normal distribution (by D'Agostino and Pearson omnibus normality test). Data for gene expression on day 2 and day 14 after transfection were analyzed by the two-tailed, unpaired t test. In cases where unequal variances were found (via F test), Welch's correction was applied. When data for one plasmid and more than two time points were compared, a 1-way ANOVA with Bonferroni's post test was used. When data for more than one plasmid and two time points were analyzed simultaneously, a 2-way ANOVA was used. Covariation of CO-CFTR expression and amount of vector DNA in lung tissue was evaluated by calculating the nonparametric Spearman correlation. Comparison of expression level and its longevity for plasmids pUCF70, pUCF80, and pUCF108 was done by first performing linear regression analysis of log-transformed geometric means for each plasmid at different time points and then comparing slopes and Y-intercepts of generated best-fit lines using an analysis of covariance (ANCOVA). For all these tests the threshold for statistical significance was set at p=0.05.

EXAMPLE 7

Development of a Validated qRT-PCR Assay

A relative quantitation assay based on real-time quantitative reverse transcription-polymerase chain reaction (qRT-PCR) is routinely used for comparison of selected target expression in different samples [37].

$$\text{Amount of target} = 2^{-\Delta\Delta Ct} \quad (1)$$

$$\Delta\Delta Ct = (Ct_{TargetA} - Ct_{InternalControl})_{Sample1} - (Ct_{TargetA} - Ct_{InternalControl})_{Sample2} \quad (2)$$

When quantitation of two targets relative to each other (A and B) is desired in the same sample, then the internal control becomes unnecessary and the ΔΔCt method can be transformed into the ΔCt method:

$$\text{Amount of target} = 2^{-\Delta Ct} \quad (3)$$

$$\Delta Ct = (Ct_{TargetA} - Ct_{TargetB}) \quad (4)$$

However, comparison of expression of two different targets with each other in the same sample is more complicated due to the potential of different target amplification efficiencies. If amplification efficiency differs, then the same amount of each target would correspond to different Ct values and would generate an error in relative quantitation.

Figure 10:
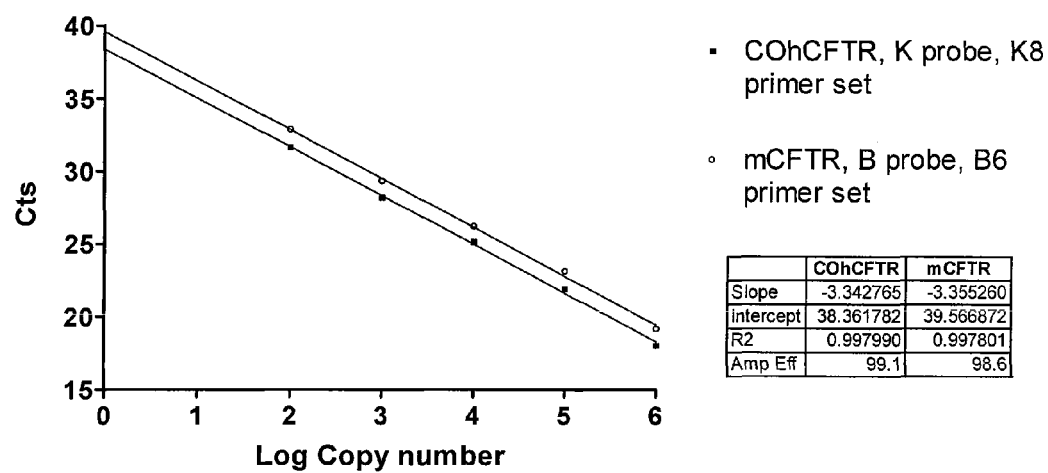
FIG. 10. Standard curves for CO-CFTR and mCFTR were generated using a validation template vector containing both genes. (Error bars are not visible due to very small variance of quadruplicate replica samples.)

In order to compare expression of endogenous mCFTR mRNA and vector derived hCFTR mRNA expression levels, we developed a variant of comparative Ct method [38] employing validated primers, probes, and template vectors. First, a vector containing both mCFTR and hCFTR (or CO-CFTR) template sequences was prepared. Using this validation template vector, standard amplification curves were generated for each target. Nine combinations of forward and reverse primers were tested for each target to select a pair of primer sets producing the most parallel amplification curves and featuring similar amplification efficiency (FIG. 10). The standard curves do not overlap, which indicates that Ct value adjustments are necessary to achieve higher precision.

These standard amplification curves can be described by linear equations (5, 6), where A and B correspond to mCFTR and CO-CFTR targets:

$$Ct_A = (\text{Slope}_A)(\text{Log}(Qty_A)) + \text{Intercept}_A \quad (5)$$

$$Ct_B = (\text{Slope}_B)(\text{Log}(Qty_B)) + \text{Intercept}_B \quad (6)$$

The Slope and Intercept values are different but constant and can be calculated from standard amplification curve analysis. The target quantity value (Qty) is the same for both targets since both standard amplification curves were generated using the identical validation vector dilutions.

$$Qty_A = Qty_B \quad (7)$$

Then Ct values obtained for one target can be adjusted to match another target using equation (8):

$$\text{Adjusted } Ct_B = ((Ct_B - \text{Intercept}_B) \times \text{Slope}_A)/\text{Slope}_B + \text{Intercept}_A \quad (8)$$

The Ct values for CO-CFTR amplification ($Ct_B$) were adjusted using equation (8) and compared to experimentally obtained Ct values for mCFTR target ($Ct_A$). The difference between $Ct_A$ and Adjusted $Ct_B$ was less than +/−0.2 Cts (see Table 3), which corresponds to +/−15% in relative expression calculations. This lack of a significant difference between $Ct_A$ and adjusted $Ct_B$, over 4 logs of template quantity, indicates that Ct values corresponding to CO-CFTR expression can be adjusted and used for quantitative comparison of CO-CFTR and mCFTR mRNA levels (equations 3 and 4).

TABLE 3

Adjustment of CO-CFTR Ct values based on standard amplification curve analysis using vectors containing CO-CFTR and mCFTR templates.

| Log Qty | CO-CFTR ($Ct_B$) | mCFTR ($Ct_A$) | Before Adjustment ΔCt = $Ct_A$ − $Ct_B$ | CO-CFTR (Adjusted $Ct_B$) | After Adjustment ΔCt = $Ct_A$ − $Ct_B$ |
|---|---|---|---|---|---|
| 6 | 18.0525 | 19.19 | 1.1375 | 19.18167546 | 0.008324543 |
| 5 | 21.9275 | 23.135 | 1.2075 | 23.07115991 | 0.06384009 |
| 4 | 25.1400 | 26.2025 | 1.0625 | 26.29566799 | −0.09316799 |
| 3 | 28.1900 | 29.3475 | 1.1575 | 29.35706866 | −0.009568657 |
| 2 | 31.6233 | 32.8575 | 1.234166667 | 32.80323553 | 0.054264473 |

This approach was used for all mCFTR, hCFTR, and CO-CFTR qRT-PCR assays. Further, hCFTR (or CO-CFTR) mRNA expression is presented as an hCFTR/mCFTR expression ratio multiplied by 100%.

EXAMPLE 8

Selection of Appropriate Animal Model

Initial animal experiments were performed in Balb/C mice and these studies did not produce prolonged expression of hCFTR and CO-CFTR mRNAs. If hCFTR protein is highly immunogenic in Balb/C mice, then a superimposed immune response to transfected and expressing lung epithelial cells could affect transgene expression by modulating local cytokine concentrations as well as induction of cell death. Either process could affect mRNA expression and vector DNA persistence.

Figure 11:
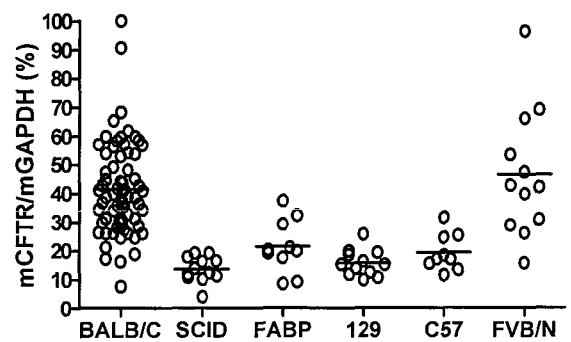
FIG. 11. Endogenous lung mCFTR/mGAPDH expression ratios. There was no significant difference in mCFTR/mGAPDH ratios between Balb/C and FVB/N mice (p=0.3693, t test), which were each higher than the other strains.

To evaluate potential immune effects, compacted DNA was dosed in T- and B-cell immunodeficient SCID and S489X/FABP-hCFTR CF mice, which express hCFTR in their gut under the control of the fatty acid binding protein promoter and therefore are tolerant to hCFTR protein (hCFTR is not expressed in their lungs). Before testing mice for CO-CFTR mRNA expression, we compared mCFTR mRNA/mGAPDH mRNA expression ratios in SCID, FABP mice, and the 3 parental strains that comprise FABP mice-129, C57, and FVB/N. Of note, the mCFTR gene in FABP mice is not functional because it is interrupted with two copies of neomycin resistance gene expression cassettes producing in-frame modification of codon 489 to produce a stop codon (S489X) [39]. Relative to normal mice, homozygous S489X mice produce only 1-2% of the normal mCFTR transcript level when using upstream primer sets (before the neomycin insertion site) [40], presumably because of increased mRNA degradation from a transcript that is translationally aberrant or other mechanisms. However, a 3' portion of the mCFTR mRNA was detected at near normal levels when using primer sets downstream from the neomycin resistance gene insertion site, likely because of hybrid transcripts originating from the pGK promoter in the neomycin resistance gene insertion site (FIG. 11 and Table 4).

TABLE 4

Expression of endogenous mCFTR in different mouse strains.

| | mCFTR/mGAPDH (%) | | | |
|---|---|---|---|---|
| | mean | SD | N | relative to Balb/C |
| Balb/c | 41.6 | 16.4 | 68 | 100% |
| SCID | 13.3 | 4.81 | 16 | 32% |
| FABP | 21.5 | 9.28 | 10 | 52% |
| 129 | 15.7 | 4.56 | 12 | 38% |
| C57 | 19.3 | 6.46 | 9 | 46% |
| FVB/N | 46.5 | 22.2 | 12 | 112% |

Figure 12:
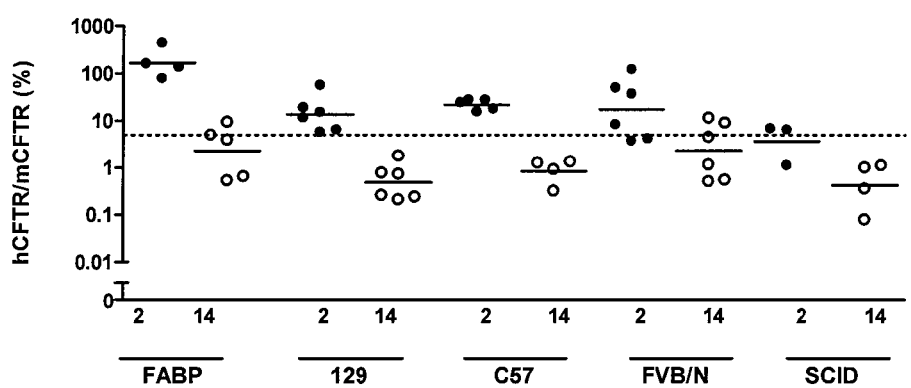
FIG. 12. Compacted pUCF2 was dosed IT (−100 m) into FABP, 129, C57, FVB/N and SCID mice. Lungs were harvested for qRT-PCR determination of hCFTR/mCFTR expression ratios at days 2 and 14. (Solid lines indicate geometric means; dotted line equals 5%.)

Each strain was dosed IT with ~100 µg of compacted pUCF2 and lungs were harvested at days 2 and 14 for qRT-PCR analysis of hCFTR/mCFTR ratios (FIG. 12). Remarkably, day 2 CO-CFTR/mCFTR geometric mean ratio in FABP mice was 167%, significantly higher than for any other strain (1-way ANOVA of log transformed data with Bonferroni's multiple comparison test), although the day 14 value fell to 2.29%. This remarkably high day 2 value is not accounted for by parental strain composition, each of which had significantly lower day 2 expression ratios. The reason for improved day 2 expression in FABP mice is unclear, although this result was reproduced amongst numerous replicate studies.

There was no persistence of CO-CFTR expression at day 14 in either SCID or FABP mice, indicating that hCFTR immunogenicity does not account for short-term expression. There was no difference in day 14 ratios amongst FABP mouse strain and its parental strains. Based on the elevated day 2 CO-CFTR expression, the FABP mouse strain was chosen as a preferred animal model for CO-CFTR expression experiments. Difference between mCFTR/mGAPDH expression ratios in Balb/C mice relative to the FABP transgenic strain was modest (1.9-fold), indicating that evaluation of hCFTR transgene expression relative to endogenous mCFTR (using downstream primers) will not be artificially elevated (more than 2-fold) due to very low mCFTR expression compared to Balb/C.

EXAMPLE 9

Detailed Analysis of the pUCF70 Vector Transcript

A polyadenylation (pA) site requires two elements to be active, an 'AAUAAA' sequence followed by a 6 nucleotide uridine rich element (URE), typically 34 to 54 ribonucleotides after the AAUAAA site [41]. Evaluation of the inverted 3' BGH transcribed sequence revealed no AAUAAA sequences. The rest of the plasmid, including the INF-β S/MAR, the prokaryotic backbone, and the β-globin S/MAR were evaluated for a transcription termination signal. Although there are no mammalian transcriptional termination signals in the prokaryotic backbone, there are AAUAAA sites in both S/MARs.

The INF-β S/MAR is variably quoted to have [30] or not to have [31] transcriptional termination activity, and these findings are likely related to the size of the S/MAR evaluated. The 800 by core fragment (used in these vectors) is cited in the literature NOT to have transcriptional termination activity [31]. This core fragment, which is contained in pUCF70, has two AATAAA sequences, but only one has a URE, and the distance between them (81 bp) is longer than typically found in transcriptional termination signals [41]. In contrast, sequence analysis of the β-globin S/MAR revealed two AATAAA sequences followed by UREs in 34 or 40 nucleotides. The prediction of this analysis is that the CO-CFTR mRNA transcript encoded by pUCF70 will terminate in the β-globin S/MAR and have a 2.3 kb 3' UTR for a total transcript size of 7.2 to 7.3 kb (assuming a polyA tail of 200 to 300 ribonucleotides). If the CO-CFTR transcript were to end in the INF-β S/MAR, however, then the total transcript would be 5.8 to 5.9 kb. These possibilities were specifically tested by performing a Northern blot from HEK293 cells transfected with pUCF70 and pUCF2 (FIG. 13). The pUCF2 plasmid serves as a control and has a predicted transcript size of 4.9 to 5.0 kb (terminates at SV40 pA site). Moreover, hybridization with a ZeoR probe tests if the pUCF70 transcript includes the prokaryotic backbone as a 3' UTR.

pUCF2 generated a 5.5 kb hCFTR transcript, which is close to the expected size of 4.9 to 5.0 kb. pUCF70 generated a 8.2 kb hCFTR transcript, which is close to the expected size of a transcript terminating at the β-globin S/MAR. The reduced intensity of the pUCF70 transcript may be due to low gel transfer efficiency, as observed with the 10 kb marker. As expected, no hybridization signal was generated for pUL transfectants. The difference between the pUCF70 and pUCF2 transcripts is 2.5 kb, which is close to the calculated difference range of 2.2 to 2.4 kb if the transcript is terminating at the β-globin S/MAR. This difference would be 0.8 to 1.0 kb if the transcript were terminating at the INF-β S/MAR. Only the pUCF70 transfectants hybridize to a ZeoR probe, as expected if this transcript terminates in the β-globin S/MAR.

In summary, these data strongly suggest that the CO-CFTR transcript in pUCF70 terminates in the β-globin S/MAR.

EXAMPLE 10

Does pUCF70 Have Episomal Replication Activity?

For pUCF70, the finding that the CO-CFTR transcript terminates in the β-globin S/MAR suggests several mechanisms that may partially explain the observed improved persistence of CO-CFTR mRNA in FABP mice. The INF-β S/MAR, when actively transcribed, has been shown to enable extrachromosomal replication of plasmid pEPI-I in dividing CHO and HeLa cells [42, 43]. Replication of pEPI-I occurs once per S-phase of the cell cycle, can initiate at many sites within the plasmid (DNA origins are sequence independent), and can persist in cells for many generations without selection pressure. Moreover, it was shown that replicating vectors are not prone to transcriptional silencing [44].

Figure 14:
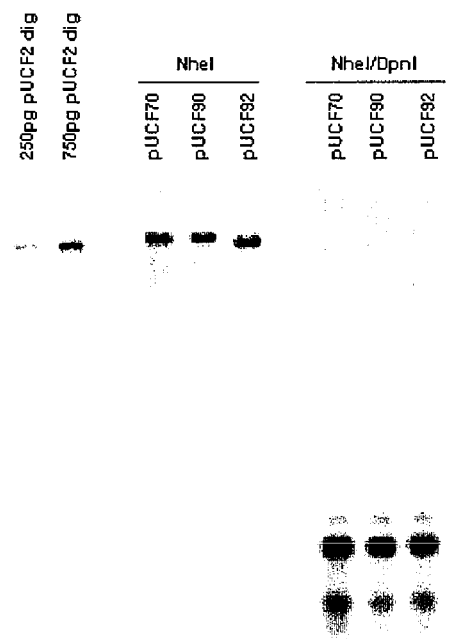
FIG. 14 Evaluation of extrachromosomal replication of plasmids pUCF70, pUCF90, and pUCF92. HeLa cells were transfected with each plasmid and on day 4 total cellular DNA was isolated. The first two lanes are plasmid pUCF2 digested with NheI. The next 3 lanes contain 0.5 µg of DNA from each transfectant digested with NheI, showing the expected sizes of the linearized vectors. The last 3 lanes contain 10 µg of DNA from each transfectant digested with NheI and DpnI; no unit length vector remains, demonstrating no evidence of extrachromosomal replication. The probe for the blot was a 1.1 kbp NcoI fragment of pUCF2, which is a common element in each plasmid.

Although surface lung epithelial cells are largely post-mitotic, a safety concern regarding pUCF70 is that low level episomal replication might occur in dividing human cells after nanoparticle dosing. Such dividing lung cells include lung stem cells and various immune cells, although gene transfer in murine alveolar macrophages is quite low [10]. To investigate whether vector pUCF70 has replication competence, log-phase HeLa cells were transfected with pUCF70 as well as derivative plasmids pUCF90 ('correctly' oriented BGH pA) and pUCF92 (lacks BGH pA) (FIG. 3). The INF-β S/MAR is actively transcribed in pUCF70 and pUCF92, but not in pUCF90. Presented in FIG. 14 is a Southern blot from HeLa transfectants. NheI linearizes each plasmid and DpnI will digest the input DNA but not newly replicated DNA (based on the methylation status of the DNA [45]). In this transient transfection assay, there was no evidence for episomal replication of any of these plasmids.

EXAMPLE 11

The NN5hCFTR gene was designed to be "nucleosome non-friendly" and hopefully less prone to silencing. This new synthetic hCFTR variant was subcloned into the pUCF70 backbone. The obtained pUCF200 plasmid was tested in tissue culture for hCFTR protein production and generated 2-3 times more protein than pUCF70. The pUCF200 plasmid was then tested in vivo to evaluate prolonged expression.

The pUCF200 compacted plasmid was dosed (IT; 6+6; 107 μg) to FABP mice. Since FABP mice were unusually old (12-16 weeks), an additional 6 mice were dosed with pUCF70 (97 μg) as a positive control. Two pUCF200 dosed mice and two pUCF70 dosed mice died before the day 2 collection. Lung samples of pUCF200 dosed mice (4+6) were collected on day 2 and 14. Lung samples of pUCF70 dosed mice were collected on day 14.

Lung samples were analyzed by RTqPCR for presence of NN5hCFTR or CO-CFTR mRNA.

Figure 15:
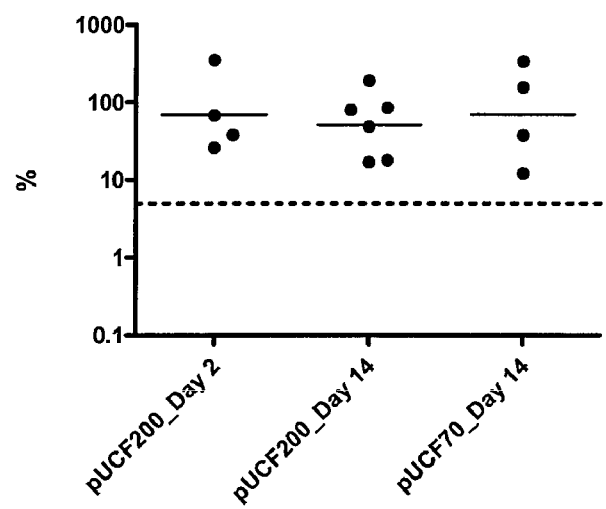
FIG. 15. The hCFTR/mCFTR expression ratio in FABP mice dosed with pUCF200 and pUCF70.

These results are shown in FIG. 15.

NN5hCFTR expression did not change from day 2 to day 14 in pUCF200 dosed animals. In addition, all pUCF200 dosed animals expressed NN5hCFTR above threshold level of 5% on day 2 and on day 14. Finally, one way ANOVA did not reveal a statistically significant difference between CO-CFTR expression on day 14 and NN5hCFTR expression on day 2 or day 14.

EXAMPLE 12

Inverted 3' BGH Transcribed Sequence Activity Evaluation: Domain Subset Analysis. Although subset regions of the inverted 3' BGH transcribed sequence could be defined arbitrarily, the results above with pUCF106 and pUCF110 suggest that single stranded DNA interactions (perhaps facilitated by DNA unwinding during transcription) may play a role in its function, similar to what has been described for the INF-β S/MAR [30,31]. Of note, hairpin structural analysis suggests that 3 distinct sense and anti-sense domains are predicted to occur within the inverted 3' BGH transcribed sequence.

Of course, this prediction is highly conjectural but does provide a basis to define roughly equal one-third regions of the inverted 3' BGH transcribed sequence for analysis. To initiate these studies, vectors pUCF102 and pUCF104 were prepared, which incorporate regions 'B+C' and region 'C', respectively (see FIGS. 3 and 16).

Plasmids pUCF102 and pUCF104 were compacted and dosed IT in FABP mice (FIG. 16). pUCF102 generated a geometric mean CO-CFTR/mCFTR ratio of 11.9% at day 2, which declined to 0.79% at day 14 (p=0.0006, t test of log transformed data). In contrast, pUCF104 generated a geometric mean CO-CFTR/mCFTR ratio of 95.6% at day 2 and 19.2% at day 14 (p=0.1492, t test of log transformed data). Interestingly, pUCF102 generated lower levels of CO-CFTR expression at day 2 than pUCF104 (p=0.0170, t test of log transformed data).

Whereas inverted 3' BGH transcribed sequence domain 'C' alone (pUCF104) was sufficient to generate prolonged CO-CFTR mRNA expression, domains 'B+C' (pUCF102) resulted in transient expression and decreased expression at day 2. Presumably, domain 'B' has a negative influence on the domain "C' mechanism, which is overcome by domain 'A' in the extended inverted 3' BGH transcribed sequence. Domain 'B' also appears to reduce CO-CFTR mRNA levels in view of the day 2 findings. These data suggest a complex underlying mechanism that may involve various protein factors that associate with these subdomains and ultimately influence CO-CFTR transcription levels.

EXAMPLE 13

Subdomain Analysis of the Inverted 3' BGH Transcribed Sequence. To define smaller domains of 'C' that might facilitate prolonged CO-CFTR mRNA expression, plasmids pUCF114 and pUCF116 were prepared, which split domain 'C' into roughly equal 5' domain 'D' (132 bp) and 3' domain 'E' (118 bp) (FIG. 17A). Compacted plasmid pUCF114 (contains 'D') and pUCF116 (contains 'E') were dosed IT in FVB/N mice and harvested at days 2 and 14 (FIG. 17B). Vector pUCF114 demonstrated maintained expression, with CO-CFTR/mCFTR geometric mean ratios of 3.72% at day 2 and 4.38% at day 14 (p=0.8311, t test of log transformed data). In contrast, pUCF116 demonstrated only transient expression, with a geometric mean ratio of 4.88% on day 2 and 1.09% on day 14 (p=0.0305, t test of log transformed data). Hence, 132 by domain "D" appears sufficient to facilitate prolonged CO-CFTR mRNA expression.

Figure 18:
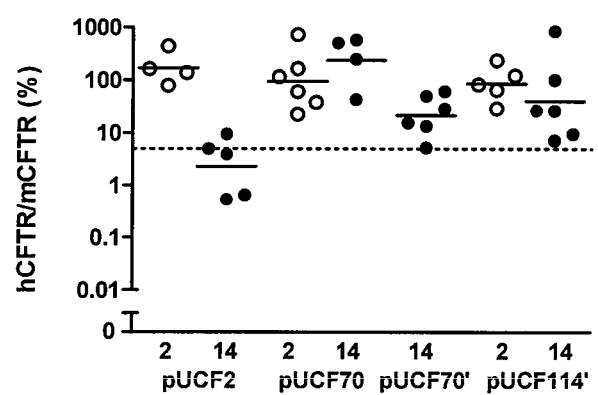
FIG. 18 Second pUCF114' study in FABP mice demonstrates maintained expression. FABP mice were dosed IT with 107 µg of compacted DNA and animal lungs were harvested at days 2 (n=5) or 14 (n=6) for qRT-PCR analysis. For comparison are prior results in FABP mice for pUCF2 and pUCF70. Dotted line equals 5%.

To confirm this result, FABP mice were dosed IT with compacted pUCF114. Lungs were harvested at days 2 and 14 for qRT-PCR analysis (FIG. 18). The hCFTR/mCFTR geometric mean ratio was 85.0% on day 2 and 39.9% on day 14 (p=0.3979, t test of log transformed data). These data confirm the initial findings in FVB/N mice, indicating that subdomain 'D' is sufficient to facilitate maintained CO-CFTR mRNA expression.

The data regarding the domains are summarized below:

| Plasmid/strain | Included domains | day 2* (%) | day 14* (%) | day 14/day 2 (%) | p-value‡ |
|---|---|---|---|---|---|
| pUCF2/FABP | none | 167.2 | 2.289 | 1.37 | 0.0006 |
| pUCF70/FABP | A, B, D**, E** | 94.08 | 235.5 | 250 | 0.2779 |
| pUCF102/FABP | B, D, E | 11.9 | 0.79 | 6.6 | 0.0006 |
| pUCF104/FABP | D, E | 95.6 | 19.2 | 20.1 | 0.1492 |
| pUCF114/FVB/N | D | 3.72 | 4.38 | 118 | 0.8311 |
| pUCF114/FABP | D | 85.0 | 39.9 | 46.9 | 0.3979 |
| pUCF116/FVB/N | E | 4.88 | 1.09 | 22.3 | 0.0305 |

Analysis of domains from the 3' portion BGH gene used in expression cassette

*geometric mean of hCFTR/mCFTR ratio
‡unpaired t test of log transformed day 2 and day 14 data; threshold significance is p = 0.05.
**Domains D and E are subsets of Domain C.

References

The disclosure of each reference cited is expressly incorporated herein.

1. Dorin J R, Farley R, Webb S, Smith S N, Farini E, Delaney S J, Wainwright B J, Alton E W, Porteous D J. (1996) A demonstration using mouse models that successful gene therapy for cystic fibrosis requires only partial gene correction. Gene Ther. September; 3(9):797-801.
2. Harvey B G, Leopold P L, Hackett N R, Grasso T M, Williams P M, Tucker A L, Kaner R J, Ferris B, Gonda I, Sweeney T D, Ramalingam R, Kovesdi I, Shak S, Crystal R G. (1999) Airway epithelial CFTR mRNA expression in cystic fibrosis patients after repetitive administration of a recombinant adenovirus. J Clin Invest. November; 104(9):1245-55.
3. Johnson L G, Olsen J C, Sarkadi B, Moore K L, Swanstrom R, Boucher R C. (1992) Efficiency of gene transfer for restoration of normal airway epithelial function in cystic fibrosis. Nat Genet. September; 2(1):21-5.
4. Chen X, Kube D M, Cooper M J, Davis P B. (2008) Cell surface nucleolin serves as receptor for DNA nanoparticles composed of pegylated polylysine and DNA. Mol Ther. February; 16(2):333-42.
5. Liu G, Li D, Pasumarthy M K, Kowalczyk T H, Gedeon C R, Hyatt S L, Payne J M, Miller T J, Brunovskis P, Fink T L, Muhammad O, Moen R C, Hanson R W, Cooper M J. (2003) Nanoparticles of compacted DNA transfect postmitotic cells. J Biol Chem. August 29; 278(35):32578-86.
6. Fink T L, Klepcyk P J, Oette S M, Gedeon C R, Hyatt S L, Kowalczyk T H, Moen R C, Cooper M J. (2006) Plasmid size up to 20 kbp does not limit effective in vivo lung gene transfer using compacted DNA nanoparticles. Gene Ther. July; 13(13):1048-51.
7. Ziady A G, Gedeon C R, Muhammad O, Stillwell V, Oette S M, Fink T L, Quan W, Kowalczyk T H, Hyatt S L, Payne J, Peischl A, Seng J E, Moen R C, Cooper M J, Davis P B. (2003) Minimal toxicity of stabilized compacted DNA nanoparticles in the murine lung. Mol Ther. December; 8(6):948-56.
8. ASGT presentation: "Highly Effective DNA Nanoparticles for Intrapulmonary Gene Delivery." 2004 Education Workshop Session. Non-Viral: Development and Application of Non-Viral Vectors, American Society of Gene Therapy Minneapolis, Minn.
9. Konstan M W, Davis P B, Wagener J S, Hilliard K A, Stern R C, Milgram L J, Kowalczyk T H, Hyatt S L, Fink T L, Gedeon C R, Oette S M, Payne J M, Muhammad O, Ziady A G, Moen R C, Cooper M J. (2004) Compacted DNA nanoparticles administered to the nasal mucosa of cystic fibrosis subjects are safe and demonstrate partial to complete cystic fibrosis transmembrane regulator reconstitution. Hum Gene Ther. December; 15(12): 1255-69.
10. Ziady A G, Gedeon C R, Miller T, Quan W, Payne J M, Hyatt S L, Fink T L, Muhammad 0, Oette S, Kowalczyk T, Pasumarthy M K, Moen R C, Cooper M J, and Davis P B. (2003) Transfection of airway epithelium by stable PEGylated poly-L-lysine DNA nanoparticles in vivo. Mol Ther. (6):936-947.
11. Rawlins E L, Hogan B L (2008) Am J Physiol Lung Cell Mol Physiol. May 16. [Epub ahead of print] Ciliated epithelial cell lifespan in the mouse trachea and lung.
12. Chen P, Tian J, Kovesdi I, Bruder J T. (2008) Promoters influence the kinetics of transgene expression following adenovector gene delivery. J Gene Med. February; 10(2): 123-31.
13. Razin A. (1998) CpG methylation, chromatin structure and gene silencing—a three-way connection. The EMBO Journal 17, 4905-4908.
14. Yew N S. (2005) Controlling the kinetics of transgene expression by plasmid design. Adv Drug Deliv Rev. April 5; 57(5):769-80
15. Hodges B L, Taylor K M, Joseph M F, Bourgeois S A, Scheule R K. (2004) Long-term transgene expression from plasmid DNA gene therapy vectors is negatively affected by CpG dinucleotides. Mol Ther. August; 10(2):269-78.
16. Hyde S C, Pringle I A, Abdullah S, Lawton A E, Davies L A, Varathalingam A, Nunez-Alonso G, Green A M, Bazzani R P, Sumner-Jones S G, Chan M, Li H, Yew N S, Cheng S H, Boyd A C, Davies J C, Griesenbach U, Porteous D J, Sheppard D N, Munkonge F M, Alton E W, Gill D R. (2008) CpG-free plasmids confer reduced inflammation and sustained pulmonary gene expression. Nat Biotechnol. May; 26(5):549-51.
17. Goetze S, Baer A, Winkelmann S, Nehlsen K, Seibler J, Maass K, Bode J. (2005) Performance of genomic bordering elements at predefined genomic loci. Mol Cell Biol. March; 25(6):2260-72.
18. Gill D R, Smyth S E, Goddard C A, Pringle I A, Higgins C F, Colledge W H, and Hyde S C. (2001) Increased persistence of lung gene expression using plasmids containing the ubiquitin C or elongation factor 1alpha promoter. Gene Ther. 8(20):1539-1546.
19. Baudouin-Legros M, Hinzpeter A, Jaulmes A, Brouillard F, Costes B, Fanen P, and Edelman A (2005) Cell-specific posttranscriptional regulation of CFTR gene expression via influence of MAPK cascades on 3'UTR part of transcripts. Am J Physiol Cell Physiol. 289(5), C1240-1250.
20. Kudla G, Lipinski L, Caffin F, Helwak A, Zylicz M. (2006) High guanine and cytosine content increases mRNA levels in mammalian cells. PLos Biology, V.6., p. 933-942.
21. Vinogradov A E (2003) Isochores and tissue-specificity. Nucleic Acids Res., V.31, N.7., p. 1838-1844.
22. Jenke A C, Stehle I M, Herrmann F, Eisenberger T, Baiker A, Bode J, Fackelmayer F O, Lipps H J. (2004) Nuclear scaffold/matrix attached region modules linked to a transcription unit are sufficient for replication and maintenance of a mammalian episome. Proc Natl Acad Sci USA. August 3; 101(31):11322-7.
23. Armentano D, Zabner J, Sacks C, Sookdeo C C, Smith M P, St George J A, Wadsworth S C, Smith A E, Gregory R J. (1997) Effect of the E4 region on the persistence of transgene expression from adenovirus vectors. J. Virol. March; 71(3):2408-16.

24. Rejman J, Bragonzi A and Conese M (2005) Role of Clathrin- and Caveolae-Mediated Endocytosis in Gene Transfer Mediated by Lipo- and Polyplexes. Molecular Therapy 12: 468-474.
25. Tousignant J D, Zhao H, Yew N S, Cheng S H, Eastman S J, Scheule R K. DNA sequences in cationic lipid:pDNA-mediated systemic toxicities. Hum Gene Ther. 2003 Feb. 10; 14(3):203-14.
26. Chen Z Y, Riu E, He C Y, Xu H, Kay M A. (2008) Silencing of episomal transgene expression in liver by plasmid bacterial backbone DNA is independent of CpG methylation. Mol Ther. March; 16(3):548-56.
27. Bradbury N A, Jilling T, Berta G, Sorscher E J, Bridges R J, and Kirk K L (1992) Regulation of plasma membrane recycling by CFTR. Science 256(5056):530-532.
28. Barasch J, Kiss B, Prince A, Saiman L, Gruenert D, and al-Awqati Q. (1991) Defective acidification of intracellular organelles in cystic fibrosis. Nature 352(6330):70-73.
29. Stehle I M, Postberg J, Rupprecht S, Cremer T, Jackson D A, and Lipps H J. (2007) Establishment and mitotic stability of an extra-chromosomal mammalian replicon. BMC Cell Biol. 8:33 (doi:10.1186/1471-2121-8-33).
30. Bode J, Kohwi Y, Dickinson L, Joh T, Klehr D, Mielke C, and Kohwi-Shigematsu T. (1992) Biological significance of unwinding capability of nuclear matrix-associating DNAs. Science 255(5041):195-197.
31. Bode J, Winkelmann S, Gotze S, Spiker S, Tsutsui K, Bi C, A K P, and Benham C. (2006) Correlations between scaffold/matrix attachment region (S/MAR) binding activity and DNA duplex destabilization energy. J Mol Biol. 358(2):597-613.
32. Riu E, Chen Z Y, Xu H, He C Y, Kay M A. (2007) Histone modifications are associated with the persistence or silencing of vector-mediated transgene expression in vivo. Mol Ther. July; 15(7):1348-55.
33. Al-Dosari M, Zhang G, Knapp J E, Liu D. (2006) Evaluation of viral and mammalian promoters for driving transgene expression in mouse liver. Biochem Biophys Res Commun. January 13; 339(2):673-8. Epub 2005 Nov. 21.
34. Brooks A R, Harkins R N, Wang P, Qian H S, Liu P, Rubanyi G M. (2004) Transcriptional silencing is associated with extensive methylation of the CMV promoter following adenoviral gene delivery to muscle. J Gene Med. April; 6(4):395-404.
35. Chung, J. H., Whiteley, M., and Felsenfeld, G. (1993) A 5' element of the chicken β-globin domain serves as an insulator in human erythroid cells and protects against position effect in Drosophila. Cell 74: 505-514
36. Molecular Cloning: A Laboratory Manual (Second Edition) By J. Sambrook, E. F. Fritsch, T. Maniatis (1989) Cold Spring Harbor, N.Y.: Cold Spring Harbor Laboratory Press, 3 v, 1659 pp.
37. Livak K J and Schmittgen T D. (2001) Analysis of relative gene expression data using real-time quantitative PCR and the $2^{-\Delta\Delta CT}$ method. Methods 25: 402-408.
38. Schmittgen T D and Livak K J (2008) Analyzing real-time PCR data by the comparative CT method. Nature Protocols 3: 1101-1108.
39. Koller B H, Kim H S, Latour A M, Brigman K, Boucher R C, Scambler P, Wainwright B, Smithies O. (1991) Toward an animal model of cystic fibrosis: targeted interruption of exon 10 of the cystic fibrosis transmembrane regulator gene in embryonic stem cells. Proc. Natl. Acad. Sci. USA. 88(23):10730-10734.
40. Snouwaert J N, Brigman K K, Latour A M, Malouf N N, Boucher R C, Smithies 0, and Koller B H. (1992) An animal model for cystic fibrosis made by gene targeting. Science. 257(5073):1083-1088.
41. Chen F, MacDonald C C, and Wilusz J. Cleavage site determinants in the mammalian polyadenylation signal. Nucleic Acids Res. 23(14):2614-2620, 1995.
42. Stehle I M, Scinteie M F, Baiker A, Jenke A C, and Lipps H J. Exploiting a minimal system to study the epigenetic control of DNA replication: the interplay between transcription and replication. Chromosome Res. 11(5):413-421, 2003.
43. Schaarschmidt D, Baltin J, Stehle I M, Lipps H J, and Knippers R. An episomal mammalian replicon: sequence-independent binding of the origin recognition complex. EMBO J. 23(1):191-201, 2004.
44. Jenke A C, Scinteie M F, Stehle I M, Lipps H J. (2004) Expression of a transgene encoded on a non-viral episomal vector is not subject to epigenetic silencing by cytosine methylation. Mol Biol Rep. 2004 June; 31(2):85-90.
45. Cooper M J, Lippa M, Payne J M, Hatzivassiliou G, Reifenberg E, Fayazi B, Perales J C, Morrison L J, Templeton D, Piekarz R L, and Tan J. Safety-modified episomal vectors for human gene therapy. Proc Natl Acad Sci USA. 94(12):6450-6455, 1997.

We claim:

1. A nucleic acid molecule comprising a portion, wherein said portion comprises at least 50 nt of SEQ ID NO: 1, wherein said portion is operably linked to a promoter from which transcription of the portion is initiated, wherein the portion is in inverted transcriptional orientation relative to its orientation in the bovine growth hormone (BGH) gene, wherein when the nucleic acid molecule further comprises a transgene operably linked to the promoter and located between the promoter and the portion, the portion improves long-term expression of the transgene.

2. The nucleic acid molecule of claim 1 wherein the portion comprises untranslated sequences of the BGH gene.

3. The nucleic acid molecule of claim 1 wherein the portion comprises translated sequences of the BGH gene.

4. The nucleic acid molecule of claim 1 which spans the 3' end of the open reading frame of the bovine growth hormone (BGH) gene and comprises both translated and untranslated sequences of the BGH gene.

5. The nucleic acid molecule of claim 1 wherein the portion comprises the sequence shown in SEQ ID NO: 1.

6. The nucleic acid molecule of claim 1 wherein the portion comprises the sequence shown in SEQ ID NO: 2.

7. The nucleic acid molecule of claim 1 wherein the portion consists of the sequence shown in SEQ ID NO: 1.

8. The nucleic acid molecule of claim 1 wherein the portion comprises the sequence shown in SEQ ID NO: 5.

9. The nucleic acid molecule of claim 1 wherein the nucleic acid further comprises a transgene.

10. The nucleic acid molecule of claim 9 wherein the transgene is shown in SEQ ID NO: 3.

11. The nucleic acid molecule of claim 9 wherein the transgene is shown in SEQ ID NO: 4.

12. The nucleic acid molecule of claim 1 wherein a restriction endonuclease site for inserting a transgene is 3' of the promoter and 5' of the portion.

13. The nucleic acid molecule of claim 1 wherein the promoter is selected from the group consisting of human beta-actin, human polyubiquitin C, and SV40.

14. The nucleic acid molecule of claim 1 which is an expression vector.

15. The nucleic acid molecule of claim 1 which is a viral vector.

16. The nucleic acid molecule of claim 1 wherein the portion is between 50 and 150 bases in length.

17. The nucleic acid molecule of claim 1 wherein the portion is between 100 and 200 bases in length.

18. The nucleic acid molecule of claim 1 wherein the portion is between 100 and 1000 bases in length.

19. The nucleic acid molecule of claim 1 which is compacted to form a DNA nanoparticle.

20. A method of improving long-term expression of a transgene in a nucleic acid molecule, comprising:
inserting into the nucleic acid molecule a portion comprising at least 50 nt of SEQ ID NO: 1, so that it is operably linked to a promoter from which transcription of the portion is initiated, wherein the portion is in inverted orientation relative to its orientation in the BGH gene and wherein the transgene is operably linked to the promoter between the promoter and the portion.

21. The nucleic acid molecule of claim 1 wherein the portion consists of the sequence shown in SEQ ID NO: 2.

22. The nucleic acid molecule of claim 1 wherein the portion consists of the sequence shown in SEQ ID NO: 5.

* * * * *